US010980952B2

(12) United States Patent
Wixey et al.

(10) Patent No.: US 10,980,952 B2
(45) Date of Patent: Apr. 20, 2021

(54) UNIVERSAL CANNULA SEAL

(71) Applicant: Intuitive Surgical Operations, Inc., Sunnyvale, CA (US)

(72) Inventors: Matthew A. Wixey, San Jose, CA (US); William A. Burbank, Sandy Hook, CT (US); Robert C. Reid, Fairfield, CT (US); Nathan A. Venskytis, Hamden, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 723 days.

(21) Appl. No.: 15/592,910

(22) Filed: May 11, 2017

(65) Prior Publication Data

US 2017/0325799 A1   Nov. 16, 2017

Related U.S. Application Data

(60) Provisional application No. 62/335,980, filed on May 13, 2016.

(51) Int. Cl.
| | |
|---|---|
| *A61B 17/34* | (2006.01) |
| *A61B 17/02* | (2006.01) |
| *A61M 13/00* | (2006.01) |
| *A61B 34/37* | (2016.01) |

(52) U.S. Cl.
CPC .......... *A61M 13/003* (2013.01); *A61B 34/37* (2016.02); *A61B 17/0293* (2013.01)

(58) Field of Classification Search
CPC .. A61M 13/003; A61B 34/37; A61B 17/0293; A61B 17/02; A61B 17/0218; A61B 17/3423; A61B 17/34; A61B 17/3417; A61B 2017/3419; F16J 15/022

USPC ......................................... 600/201, 204, 208
See application file for complete search history.

(56) References Cited

U.S. PATENT DOCUMENTS

| | | |
|---|---|---|
| 5,209,737 A | 5/1993 | Ritchart et al. |
| 5,304,143 A | 4/1994 | Green et al. |
| 5,603,702 A * | 2/1997 | Smith ................ A61B 17/3462 251/149.1 |
| 6,726,699 B1 | 4/2004 | Wright et al. |
| 6,945,983 B2 | 9/2005 | Dittrich et al. |
| 7,988,672 B2 | 8/2011 | Heinrich |
| 8,562,569 B2 | 10/2013 | Hart et al. |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Jessica Weiss
(74) *Attorney, Agent, or Firm* — Schwegman Lundberg & Woessner, P.A.

(57) ABSTRACT

A medical device can include a housing, a first seal structure, and a seal expander. The first seal structure can have a proximal end and a distal end, and a side wall surrounding and defining an interior chamber. A seal wall can be connected to the side wall and include an expandable opening. A seal expander can be coupled to the housing, and can be at least partially in the interior chamber of the first seal structure. The seal expander can include an expandable neck portion and a seal interface portion, the seal interface portion being near an intersection of the side wall and the seal wall.

18 Claims, 21 Drawing Sheets

(56) References Cited

U.S. PATENT DOCUMENTS

| | | | |
|---|---|---|---|
| 2009/0270817 A1* | 10/2009 | Moreno | A61B 17/3462 604/264 |
| 2010/0010446 A1* | 1/2010 | Schweitzer | A61B 17/3498 604/167.01 |
| 2015/0123355 A1* | 5/2015 | Castro | F16J 15/022 277/648 |
| 2015/0223833 A1* | 8/2015 | Coffeen | A61B 17/3462 600/204 |
| 2016/0106460 A1* | 4/2016 | Farin | A61B 17/3421 600/204 |

* cited by examiner

US 10,980,952 B2

UNIVERSAL CANNULA SEAL

CLAIM OF PRIORITY

This application claims the benefit of priority under 35 U.S.C. § 119(e) to U.S. Provisional Patent Application Ser. No. 62/335,980, filed on May 13, 2016, which is incorporated by reference herein in its entirety.

TECHNICAL FIELD

This document relates generally to medical devices, and more particularly, to systems, devices and methods for sealing an opening in a body during a surgical procedure.

BACKGROUND

Certain surgical procedures, such as minimally-invasive or laparoscopic surgery, can involve delivery of an insufflation of a gas into the body. For example, in a laparoscopic procedure, an insufflation gas can be delivered to the peritoneal cavity of a patient to distend the abdomen and improve visual and physical access to internal organs in the abdomen. Distension of the patient's abdomen can provide sufficient operating space enable adequate visualization of the structures and manipulation of instruments inside a patient.

It is important to maintain a sealed system to maintain insufflation during a surgical procedure. For example, the interface between surgical equipment and an access orifice in the patient's body must be sealed to avoid or reduce leakage of insufflation gas so that insufflation can be maintained.

In a laparoscopic procedure, one or more cannulas are typically used to a deliver surgical tools into a body cavity. A cannula seal can be used to provide a seal between the cannula an outer surface of an instrument shaft that is connected to surgical tool to avoid or reduce leakage of insufflation gas through the cannula during the procedure. The cannula seal is a critical component for surgery in the abdomen, because without it there is no insufflation, and without insufflation surgery cannot be effectively carried out.

U.S. Pat. No. 6,945,983 discloses a sealing device with a variable central opening.

U.S. Pat. No. 5,209,737 discloses an elastomeric septum that is disposed in a trocar channel and includes portions which define an orifice having, in a relaxed state a first cross-sectional area, and an actuation assembly provided with levers which pivot radially outwardly to expand the seal and thereby expand the orifice to a second cross-sectional area in response to entry of the instrument into the channel.

SUMMARY

An example medical device seal assembly can include a housing, a first seal inside at least part of the housing, and a plurality of elongated segments that extend into the first seal. The first seal can include a side wall that surrounds and defines an interior chamber, an expandable portion that joins a distal end of the side wall, and a first opening at a proximal end of the interior chamber. The first seal can further include an expandable seal opening in the expandable portion, an axis of the interior chamber being defined between the first opening and the expandable seal opening.

The plurality of elongated segments can extend distally into the interior chamber of the first seal. Each elongated segment can include a proximal portion, a middle portion, and a distal tip. Each elongated segment can extend from the proximal portion of the elongated segment, into the interior chamber of the seal and toward the axis of the interior chamber to the middle portion, and then further into the interior chamber and away from the axis of the interior chamber to the distal tip of the elongated portion. Each distal tip of each of the plurality of elongated segments can be positioned on or near the side wall of the first seal. In some examples, the plurality of elongated segments can be arranged concentrically around the axis of the interior chamber. In some examples, each of the elongated segments can further include at least one flange that is connected to the distal tip and extends inward toward the chamber axis.

The plurality of elongated segments can converge at the middle portion to define a neck, the neck having a minimum internal neck dimension. The minimum internal neck dimension can be sized less than a selected outer cross-sectional dimension of an instrument shaft, such that, when the instrument shaft is inserted through the elongated segments, the instrument shaft biases the elongated segments away from the axis of the interior chamber to press against the side wall of the first seal and expand the expandable portion of the first seal and the seal opening.

In some examples, each of the elongated segments has a segment length in a proximal to distal direction and a segment width that varies along the length of the elongated segment. A minimum segment width can, for example, be at the middle portion of the elongated segment, and a maximum segment width can be in the proximal portion of the elongated segment.

The medical device seal assembly can further include a second seal distal of the first seal. The medical device seal assembly can also further include an extraction guide between the first seal and the second seal. The extraction guide can include including a distally-facing concave surface and an extraction guide opening in the distally-facing concave surface. The extraction guide opening can be aligned with the expandable seal opening in the first seal.

An example medical device can include a housing, a first seal structure at least partially inside the housing, and a seal expander. The first seal structure can include a proximal end and a distal end, and a side wall surrounding and defining an interior chamber, and a seal wall connected to the side wall. The first seal structure can further include a first opening at a proximal end of the side wall, and an expandable opening in the seal wall. An axis of the interior chamber can be defined between the first opening and the expandable opening.

The seal expander can be coupled to the housing and at least partially in the interior chamber of the first seal structure. The seal expander can include an expandable neck portion and a seal interface portion. The seal interface portion can be near an intersection of the side wall and the seal wall. In some examples, the seal interface portion can interface with the side wall of the first seal structure at an angle perpendicular to the axis or perpendicular to the side wall.

In some examples, the medical device can have a first state and a second state, where in the first state, the neck portion of the seal expander is in an expanded state to accommodate a shaft portion of an instrument, the neck portion having an one or more internal surfaces defining an internal profile having an expanded internal size to accommodate an outer surface of the shaft of the instrument, the seal interface portion of the seal expander being pressed against the side wall of the first seal structure, and the expandable opening in the seal wall being expanded to an expanded opening size. In a second state, the neck portion of the seal expander is in a neutral state, the internal surfaces of the neck portion defining an internal surface profile having a neutral internal size that is smaller than the expanded internal size, and the expandable opening in the seal wall having a second opening size that is smaller than the expanded opening size.

In some examples, the medical device can further include a second seal structure coupled to the housing, and an extraction guide inside the second seal structure, at least a portion of the first seal structure extending inside the extraction guide. The extraction guide can include a distally-facing surface that is distal of the expandable opening in the seal wall of the first seal structure, and an extraction guide opening in the distally-facing surface. The extraction guide opening can be aligned with the axis. The distally-facing surface can include portions sized and shaped to guide an object to the extraction guide opening.

In some examples, the seal expander includes a plurality of elongated elements that extend distally into the first seal structure, converge to form the neck portion, and extend from the neck distally and outwardly away from the axis, each of the elongated elements having one or more distal surfaces, the seal interface portion of the seal expander including the one or more distal surfaces on the elongated elements.

An example medical device includes a first seal having a side wall, a seal portion connected to the side wall, an interior chamber defined by the side wall, and a seal opening defined in the seal portion, and a plurality of elongated segments extending into the interior chamber of the first seal. The plurality of elongated segments can extend to converge at an intermediate neck, and then extend further to diverge at a distal mouth. Expansion of the intermediate neck can bias distal ends of the elongated segments radially outward against the side wall of the first seal and increase the size of the seal opening. A difference between the seal opening diameter and the neck inner diameter can define a seal offset dimension. In some examples, the plurality of elongated segments are sized and shaped to provide a consistent offset dimension seal offset dimension through a range of expanded states to accommodate a range of sizes of shafts inserted through the plurality of elongated segments.

The medical device can optionally further include base portion, each of the plurality of elongated segments being coupled to the base portion by one or more hinge portions, the plurality of elongated segments pivoting at the one or more hinge portions when the neck is expanded.

The medical device can optionally further include a cannula cap, a cannula coupled to the cannula cap, a second seal at least partially in the cannula, and an extraction guide at least partially in the second seal, the first seal being at least partially in the extraction guide. In some examples, the seal opening is circular and has a seal opening diameter, and the intermediate neck defines a circular opening having a neck inner diameter, the seal opening diameter being smaller than the neck inner diameter.

In some examples, the medical device can include a first state and a second state. In the first state, the plurality of elongated segments and the seal portion are in an expanded state to accommodate a shaft portion of an instrument, a difference between an expanded seal opening diameter and the neck inner diameter defining a first state offset dimension. In the second state, the plurality of elongated segments and the seal portion are in a neutral state, a difference between a neutral seal opening diameter and the neck inner diameter defining a second state offset dimension, the first state offset dimension being approximately the same as the second state offset dimension.

A method of sealing two instruments having different sized shaft in a cannula seal can include receiving into a cannula a first instrument having a first shaft of a first cross-sectional outer diameter, and receiving the instrument shaft into a neck portion of a seal expander, a cross-sectional dimension of an opening in the cannula seal being smaller than a cross-sectional opening in the neck portion of the seal expander by an offset dimension. The method can further include biasing outer portions of the seal expander against a side wall of a cannula seal to expand an opening in a cannula seal to accommodate the first cross-sectional outer diameter, without changing the offset dimension, and receiving the first shaft into the cannula seal and sealing against an outer surface of the first shaft.

The method can optionally further include, after the first instrument is removed from the cannula seal, receiving into the cannula a second instrument having a second shaft of a second cross-sectional outer diameter that is different than the first cross-sectional outer diameter, receiving the second shaft into the neck portion of the seal expander, and biasing the outer portions of the seal expander against the side wall of the cannula seal to expand the opening in a cannula seal to accommodate the second cross-sectional outer diameter, without changing the offset dimension.

In some examples, receiving an instrument shaft into a neck portion of a seal expander can include receiving an instrument shaft into a neck opening defined by a plurality of elongated segments that form the seal expander, the opening being smaller than the cross-sectional outer diameter of the first instrument shaft, and wherein, biasing outer portions of the seal expander against the side wall includes deflecting the elongated segments outwardly against the side wall of the cannula seal. In some examples, expanding the cannula seal includes stretching a portion of the cannula seal to enlarge an opening in the cannula seal, and receiving the first shaft into the cannula seal includes receiving the first shaft through the opening in the cannula seal.

Each of these non-limiting examples can stand on its own, or can be combined in various permutations or combinations with one or more of the other examples.

This Summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
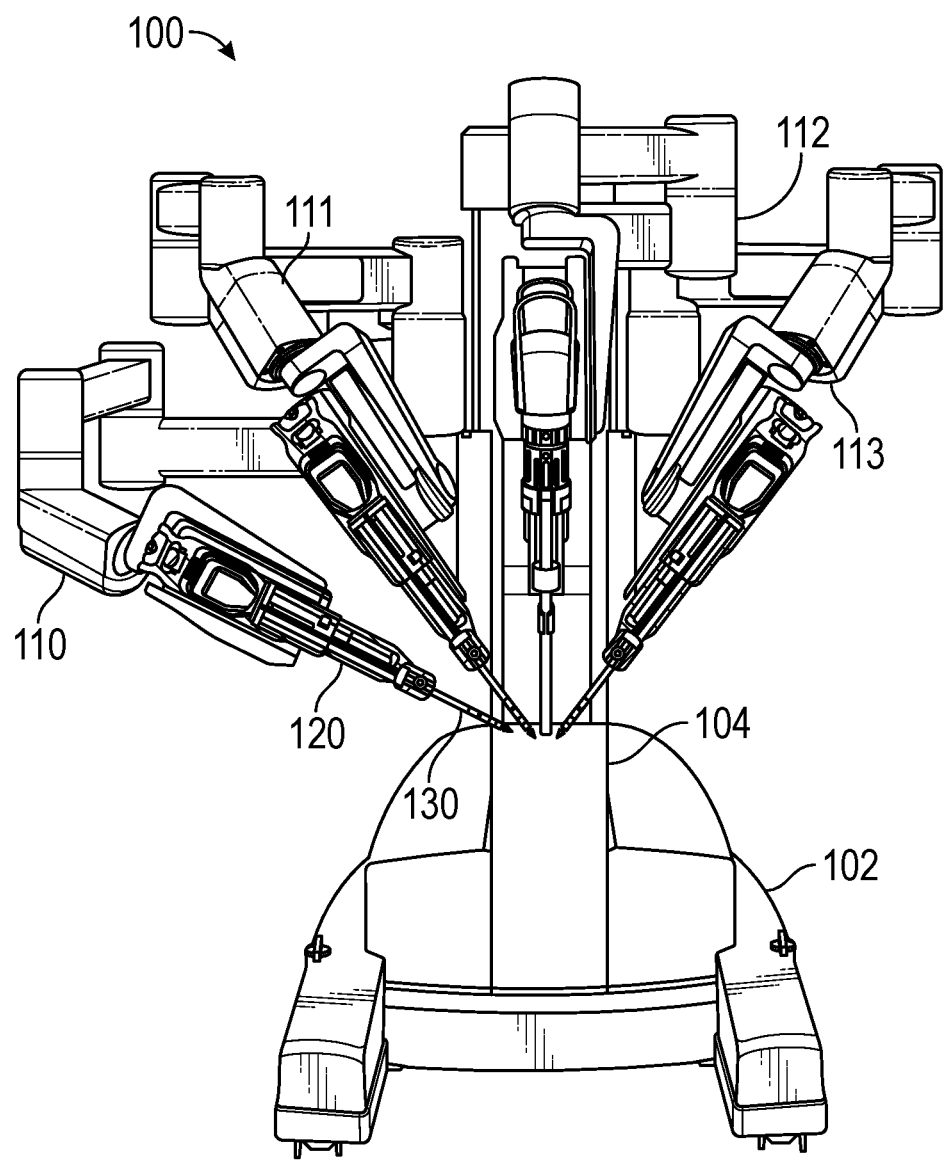
FIG. 1A is an illustration of an example instrument system for use in robot-assisted minimally invasive surgery.

A cannula seal that can accommodate a range of instrument shaft sizes can be used in a laparoscopic surgical procedure. During a laparoscopic surgery procedure in the abdomen, for example it is important that the abdomen be distended to provide space to for operation of visualization tools and surgical tools. An expandable cannula seal can be used to deliver visualization tools and surgical tools and maintain insufflation during the procedure. A cannula seal is a critical component for maintaining insufflation during minimally-invasive surgery or laparoscopic surgery. Without it there is no insufflation, and without insufflation, surgical procedure cannot be effectively carried out. Temporary loss of pressure during certain portions of the procedure is not catastrophic, as more insufflation gas can be delivered to reestablish insufflation, but preservation of installation is generally needed during the manipulation of tools as the procedure is carried out.

In some surgeries, it is desirable to exchange tools during the procedure. Exchanging tools during a procedure presents a problem, as seals are frequently designed to accommodate a particular shaft size. A mismatch between tool size and seal size can create procedural problems, such as damage to the seal or insufflation gas leaks. But switching out a cannula seal to accommodate a tool change during a procedure can be time consuming and inconvenient.

A universal cannula seal, i.e., a seal that can accommodate a range of tool sizes, can be provided to avoid the need to change the cannula or cannula seal during a procedure. For example an expanding seal assembly can include a seal, such as a wiper seal, and mechanism to that change the size of an opening in the seal, to maintain an effective seal with different sized instrument shafts.

An expanding seal assembly can include, for example, a cannula seal and a seal expander that has elements that expand a seal opening based upon the size of tool that is inserted into portion of the seal expander, such as a neck. A deflectable structure that is contacted by an outer surface of an instrument shaft can be connected or otherwise linked to a structure that contacts a portion of a seal structure. Insertion of the instrument shaft into the medical device assembly can causes movement of the deflectable structure, which in turn can expand an opening in the seal structure.

In an example, a plurality of elongated elements extend through the medical device assembly in an insertion direction, and converge at a first location to form a first inner cross-section at which an outer surface of an instrument shaft contacts inner surfaces of the elongated elements. The elongated elements can diverge from the first location and extend to a second location at which the elements interact with the seal structure. Expansion of the first location by an instrument shaft can cause a corresponding expansion at the second location, which can expand an opening in the seal structure. In an example, the elongated elements can provide an approximately one-to-one expansion ratio, e.g. a one millimeter displacement of an element at the first location causes a one millimeter displacement at the second location. Other expansion ratios are possible.

An expanding seal assembly can be used with a surgical system that includes tools that allow a physician to see and manipulate tissue (or other objects or materials) inside a patient's body, using controls situated outside the patient's body. Visualization tools can, for example, include optical tools, such as fiber optic cameras, or electronic tools, such as digital cameras or sensors. Surgical tools can include, for example mechanical or electromechanical tools such as needle drivers, suture tools, retraction instruments, clip appliers, probes fenestrated graspers, or cardiac stabilizers. Surgical tools can also include energy instruments such as monopolar or biopolar tools, ultrasonic tools, or lasers, which can be used for cautery or ablation, for example. Tools can be coupled to a computer system and electromechanical manipulators to provide precision and ease of use for a physician or clinical personnel. The use of such systems is sometimes referred to as a robot-assisted minimally invasive surgery.

Figure 1B:
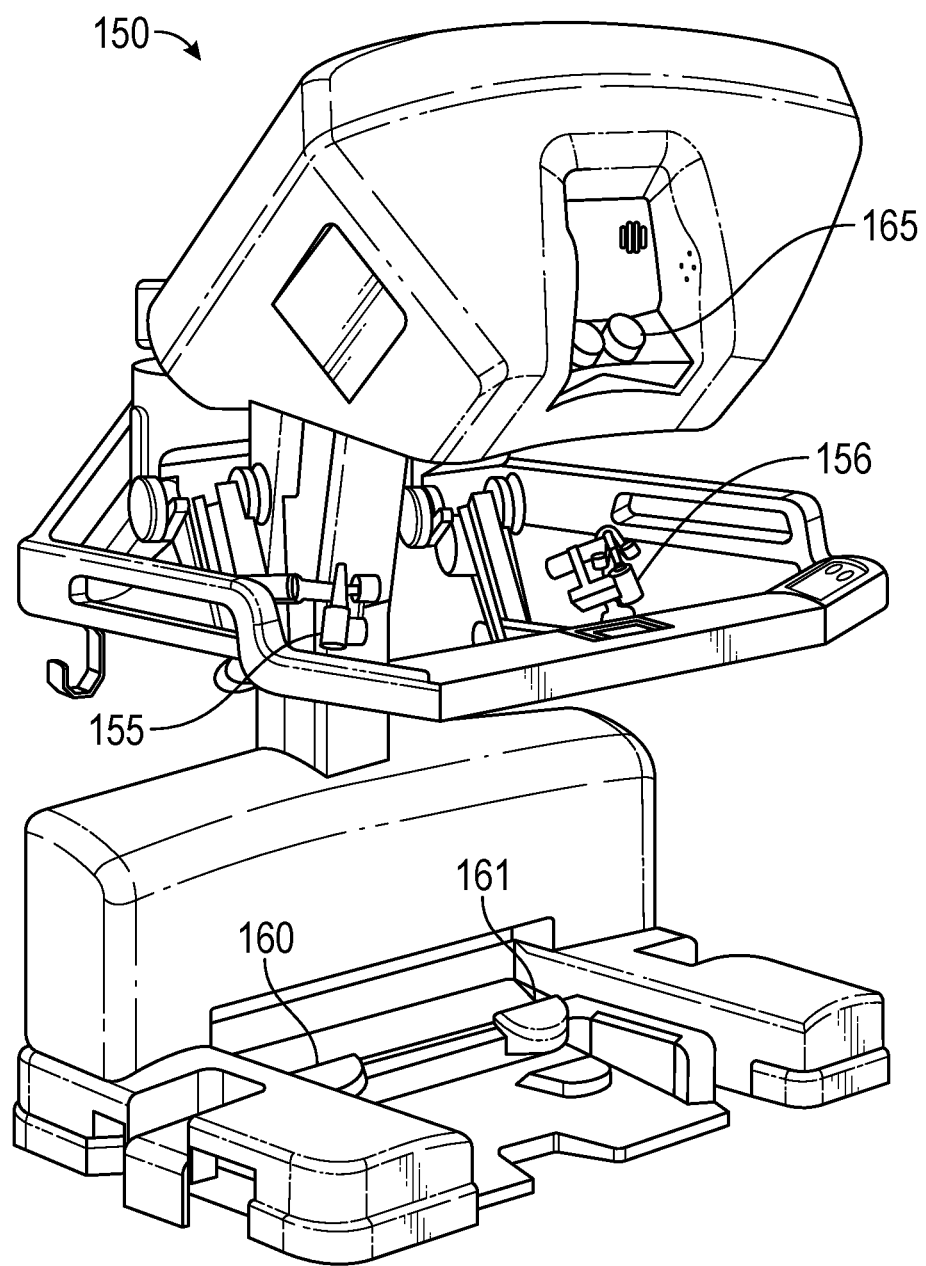
FIG. 1B is an illustration of an example physician console for use in robot-assisted minimally invasive surgery.
Figure 1C:
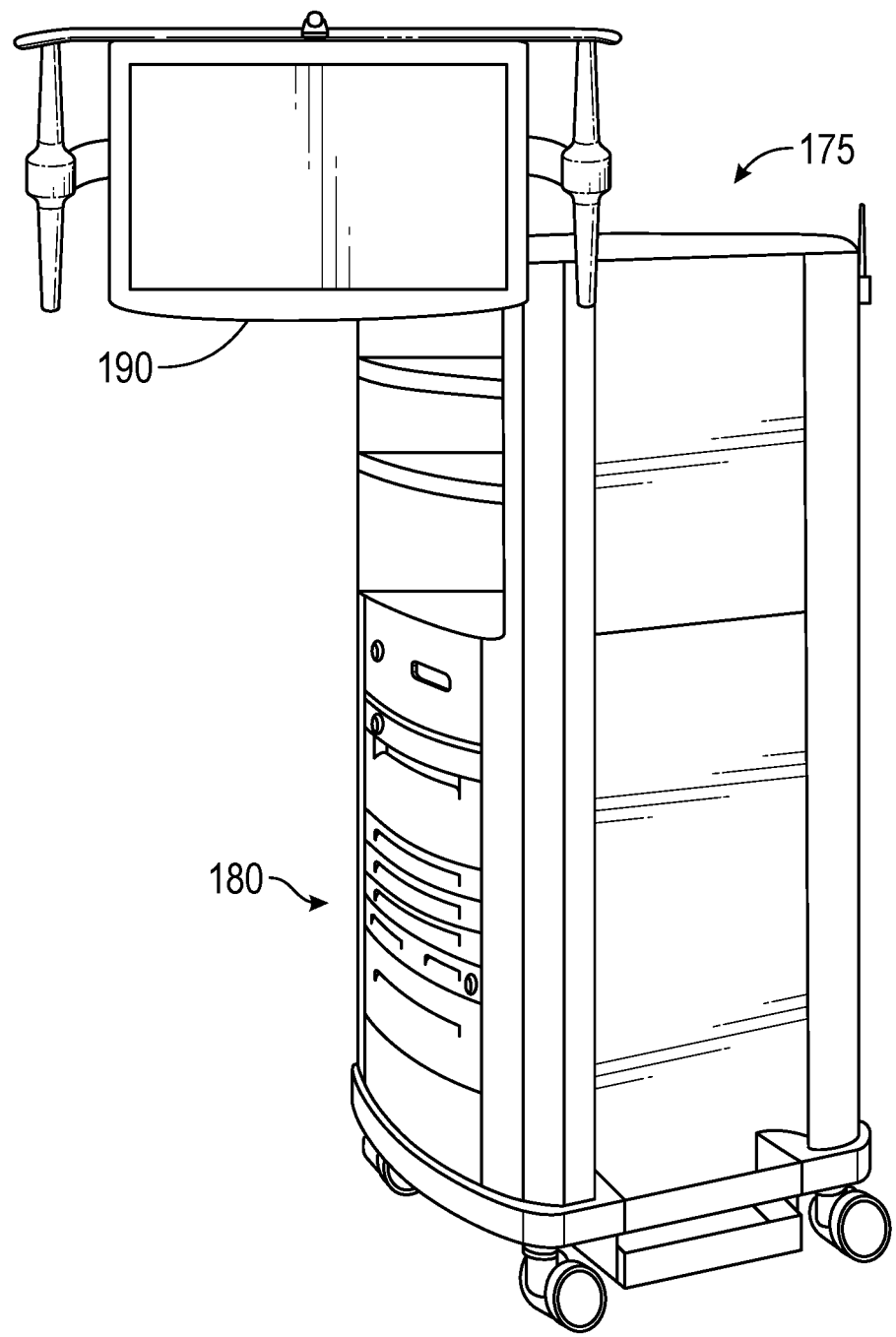
FIG. 1C is an illustration of an example control cart for use in robot-assisted minimally invasive surgery.

FIGS. 1A, 1B, and 1C, illustrate an example robot-assisted minimally invasive surgical system. FIG. 1A shows an instrument system 100 (sometimes known as a "patient side cart") that can be situated near a patient operating table (not shown). FIG. 1B shows a surgeon console 150 that can include controls and a viewing system. FIG. 1C shows a control cart 180 that can include, for example, processing equipment and communication equipment.

Referring again to FIG. 1A, the system 100 can include a base 102, a support tower 104, and one or more manipulator arms 110, 111, 112, 113, which can be mounted on the support tower. Alternatively, the manipulator arms 110, 111, 112, 113 can be connected to a main boom (not shown), which can be movable. An instrument 130 can be mounted to an instrument mount 120 on one of the manipulator arms. A cannula (not shown in FIG. 1A) can be mounted to a cannula mount. An instrument 130 can be inserted through a cannula seal in the cannula, and into the patient (not shown) for use in a surgical or other medical procedure. Through movement of the manipulator arms, the orientation of the instrument can be controlled in multiple dimensions, e.g. lateral, horizontal, vertical, angular movements in one, two, or three planes.

FIG. 1B shows an example physician console 150. The physician console can include hand control 155, 156 and pedal controls 160, 161. The hand controls 155, 156, and pedal controls 160, 161 can be used to control equipment at the patient side cart. For example, portions of a distal end of an instrument can be manipulated using instrument controls. The controls can include haptic feedback features so that a physician can interpret physical information, such as resistance or vibration, through the controls. The physician console 150 can also include a viewing system 165 that can display video or other images of a surgical site.

FIG. 1C shows an example control cart 175. The control cart can include processing equipment 180 for processing controls, facilitating communication between the physician console and the patient side cart, or a remote site. The control cart 175 can also include a display 190, which can show images that the physician is seeing on the physician console, a video feed from a camera in the patient, or other information. In an example configuration, signals input at a surgeon console 150 (also "physician console 150") can be transmitted to the equipment 180 on the control cart, which can interpret the inputs and generate commands that are transmitted to the system 100 to cause manipulation of an instrument 130 or portions of a manipulator arm 110. The equipment 180 is shown on a cart for exemplary purposes, but could also be arranged in various configurations, e.g., it could be integrated as part of the physician console, the patient side cart, or both, or divided between the physician console and patient side cart. The equipment can also be provided as software, hardware, or both, on an installed or remote system.

Figure 2A:
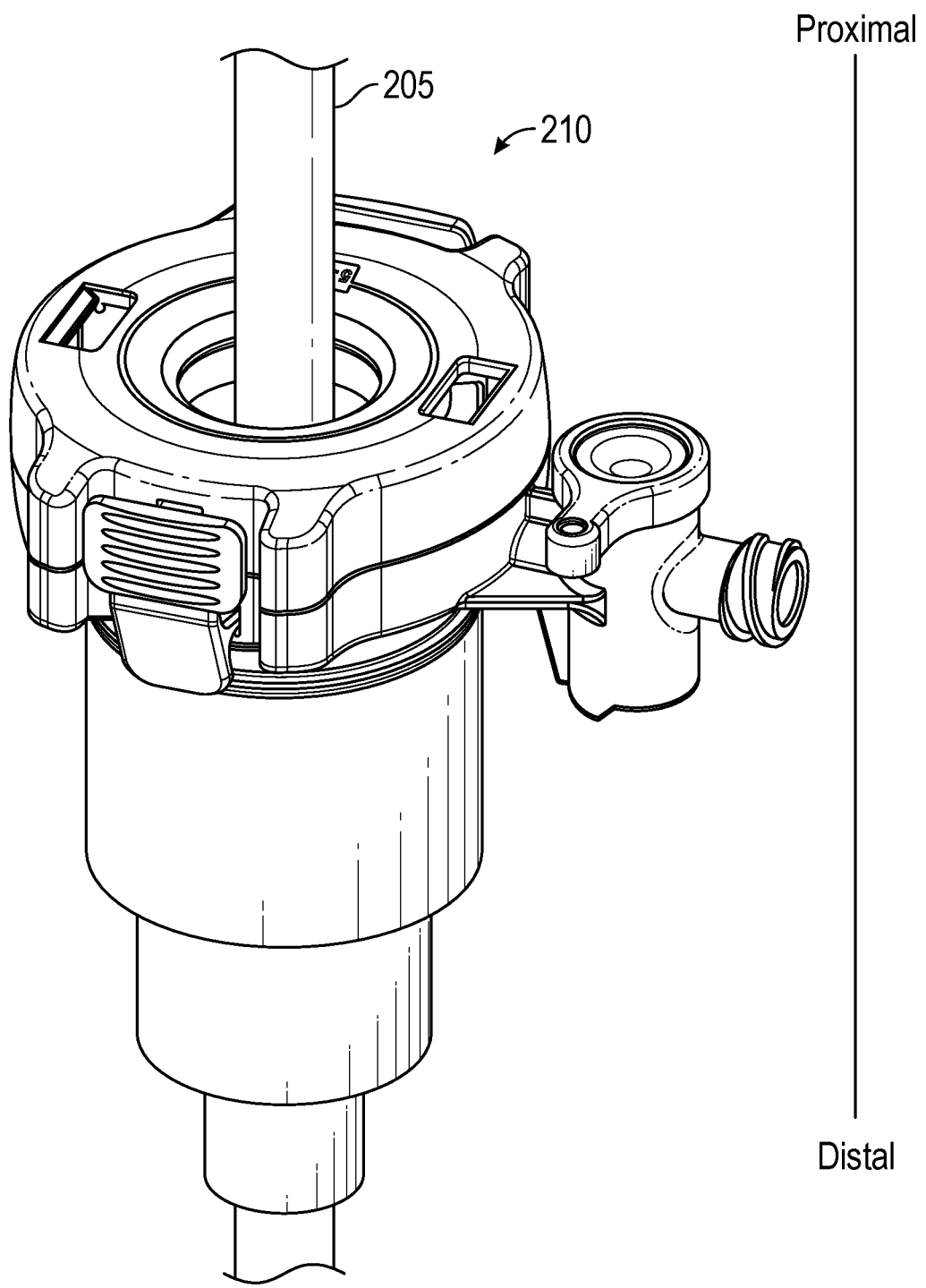
FIG. 2A is a perspective view of an example expandable seal assembly with an instrument shaft inserted through the assembly.
Figure 2B:
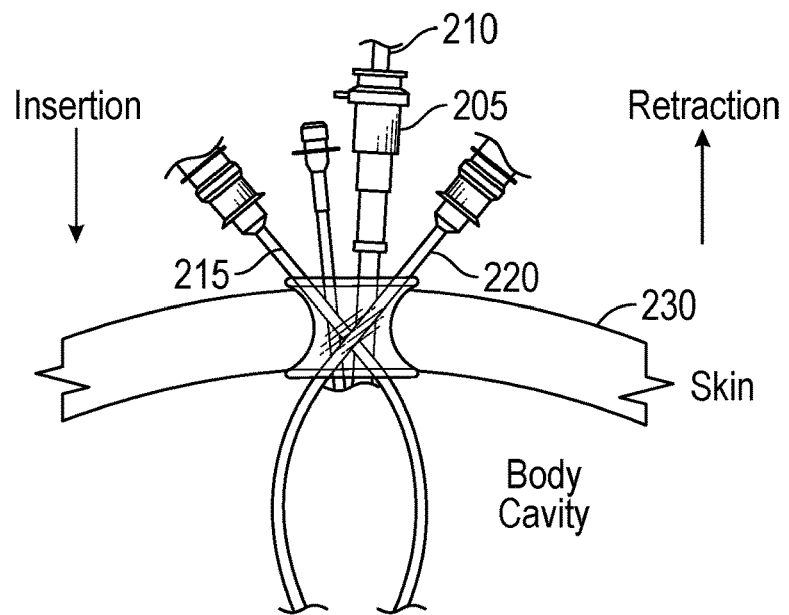
FIG. 2B is an illustration of an expandable seal assembly utilized in a minimally-invasive surgical procedure.

FIG. 2A and FIG. 2B show an example of an expandable cannula seal within a cannula 205 in a minimally invasive surgery system. An instrument shaft 210 can be inserted into through a cannula seal assembly, which includes an expandable cannula seal. The cannula seal can prevent or reduce leakage around the instrument shaft 210.

FIG. 2B shows the cannula 205 utilized in a single site surgical approach, where multiple instrument shafts can be inserted through cannulas 215, 220 that are inserted through a single incision site in the skin 230, such as through the navel. A tool such as an end effector or a visualization device can be situated on a distal end of an instrument shaft that is inserted through an expandable cannula seal. An end effector utilized in the surgical system can be a jawed surgical end effector, such as a scissors, grasping retractor, or needle driver, for example. A visualization device can be a digital video camera or endoscope, for example. An expandable cannula seal can allow for exchange of instruments during the procedure without changing the cannula seal, even if the instruments require or include shafts of varying dimensions, because the cannula seal can expand to accommodate different shaft sizes.

FIG. 3A-3F show an example medical device seal assembly 300 that can include an expandable seal that accommodates a range of instrument sizes. The medical device seal assembly 300 can include a cap 305, a seal expander 310, a first seal 315, a retraction guide 320, a clip 325, a second seal 330, and a housing 340. Elongated segments 391, 392, 393, 394, 395, 396 on the seal expander 310 can be deflected by outer surfaces of an instrument shaft. The elongated segments 391, 392, 393, 394, 395, 396 can stretch the first seal 315 to expand an opening in the seal, to accommodate insertion of an instrument shaft through the seal assembly 300.

Figure 8:
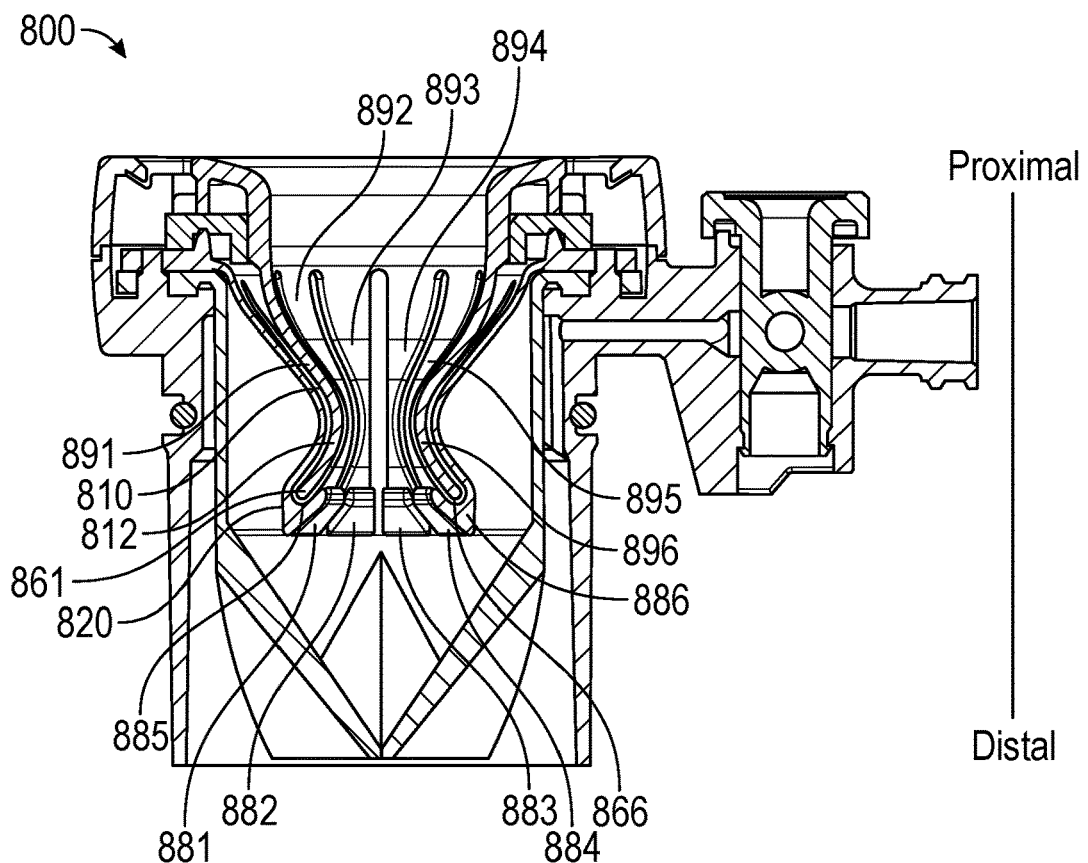
FIG. 8 is a cross-sectional view of an example seal assembly without a first seal between the expander and retraction guide.
Figure 9:
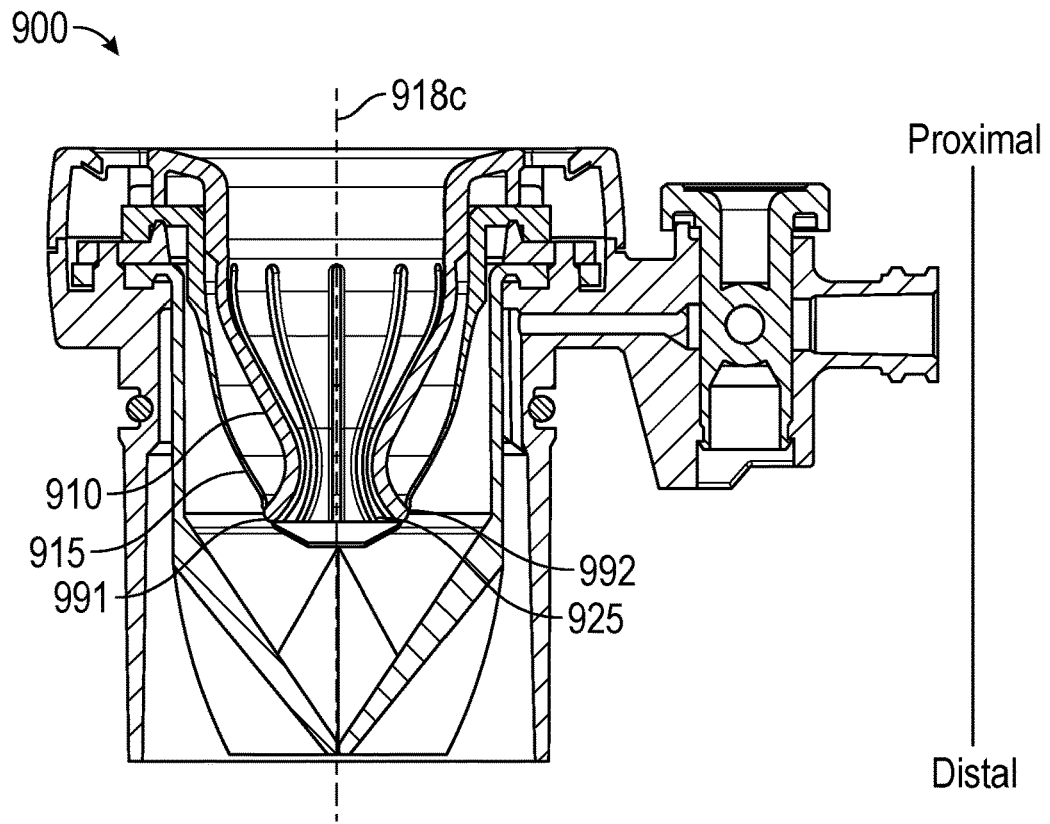
FIG. 9 is a cross-sectional view of an example seal assembly that does not have a retraction guide.
Figure 10:
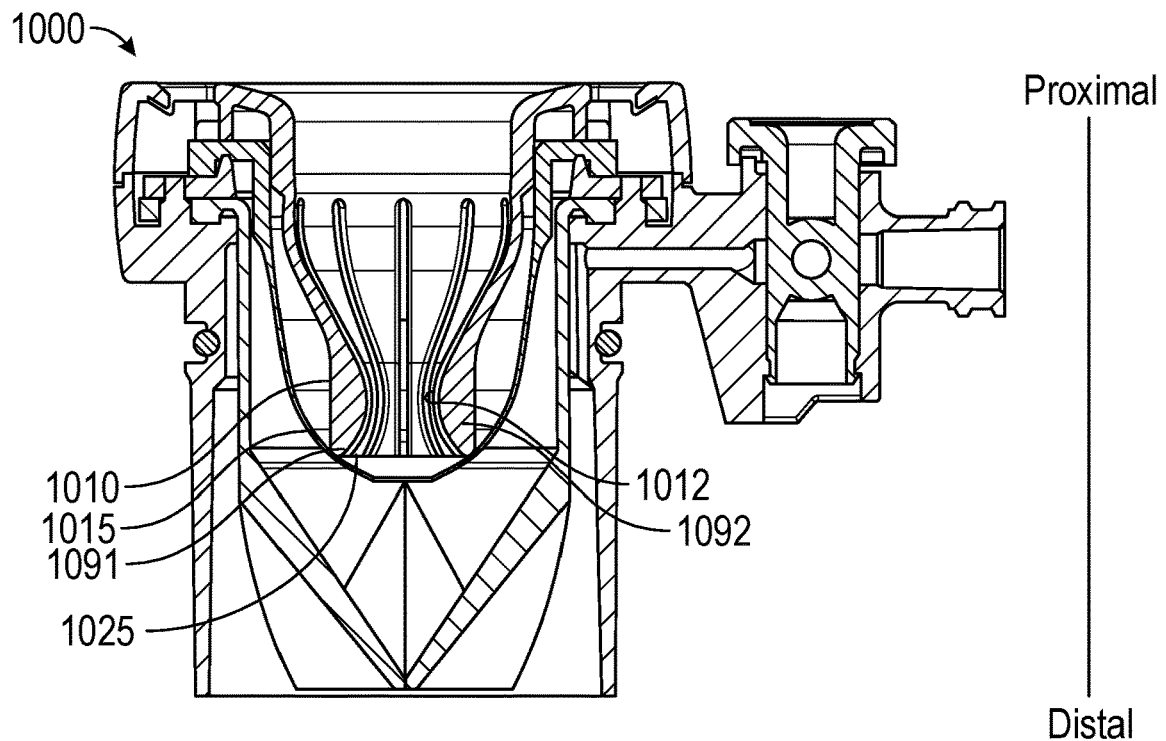
FIG. 10 is a cross-sectional view of an example seal assembly that has a straight-walled expander.

The seal expander 310, first seal 315, retraction guide 320, second seal 330, and housing 340 can be assembled, from proximal to distal (shown in the exploded view provided in FIG. 3C), with each part fitting at least partially into the next part, i.e. the seal expander 310 can at least partially be inserted into the first seal 315, which can be inserted into the retraction guide 320, which can be inserted into the second seal 330, which can be inserted into the housing 34. The components can be held together by the cap 305 and clip 325. In some examples, the medical device seal assembly can include a subset of the parts shown in FIGS. 3A-3F. For example, the retraction guide 320 could be omitted, as shown in FIG. 8, FIG. 9, and FIG. 10, or the second seal 330 could be omitted.

The cap 305 can include an opening 306 and a label 307 that indicates a range of sizes (e.g. 5-14 mm) that are compatible with the expandable seal system. The cap can be formed of a rigid material, such as polycarbonate.

The seal expander 310 can include a proximal opening 311, an expandable neck portion 312, and a distal mouth 313. The seal expander can, for example, be formed of polycarbonate. The seal expander 310 can also include an expander proximal lip 314 that can rest or seal against the cap 305. Inner surfaces 349 of the seal expander 310 can be shaped to act as an insertion guide to guide a tool into the seal expander. For example, the inner surfaces can be shaped like a funnel that extends from a proximal opening 318a to neck portion 312 of the seal expander 310.

The neck portion 312 of the seal expander 310 can expand when an instrument shaft is inserted into the neck. In an example, the neck portion can expand so that an expanded inner diameter of the neck portion 312 matches an inner diameter of the proximal opening 318a.

The first seal 315 (also shown in FIGS. 5B and 5C) can include a side wall 317 that defines an interior chamber 319. The distal opening 318b can be sized and shaped to seal against an instrument shaft inserted through the opening. The first seal 315 can, for example, be a wiper seal. The side wall 317 can be define portions of a cylinder, frustum, curve-walled funnel, bell-shaped flare, or polygonal prism, for example. The first seal 315 can also include portions that define a proximal opening 318a and a distal opening 318b, which together define an axis 318c of the interior chamber 319. The first seal can also include proximal lip 316 sized and shaped to rest or seal against the proximal lip 314 of the seal expander, against the cap 305, or against both the cap 305 and the proximal lip 314. For example, the proximal lip 314 of the seal expander 310 and the proximal lip of the first seal 315 can be shaped as rings with overlapping diameters, i.e. the outer diameter of the proximal lip 314 of the seal expander 310 can be larger than the inner diameter of the proximal lip 316 of the first seal 315 so that the rings overlap. The first seal can be made, for example, of polyisoprene, with a durometer of 37 to 48. The side wall 317 of the first seal 315 can vary in thickness proximally to distally. For example, a proximal portion can be relatively thick, e.g. 1-2 mm, to provide strength near the proximal lip. A distal portion 354 that forms the distal opening 318b can be relatively thin, e.g. less than 0.1 mm, to allow the seal to stretch and expand the distal opening 318b.

The medical device seal assembly 300 can also include an extraction guide 320. The extraction guide can, for example, be formed of low density polyethylene (LDPE). The extraction guide can include a proximal opening 322, walls sized and shaped to define an interior chamber that can receive the first seal, and a distal opening 321. The extraction guide can include one or more inwardly tapered or concave distal surfaces 323 that can guide awkwardly-shaped objects, such as gauze or tissue, or other object such as tools, to the distal opening 321 during retraction. For example, the extraction guide can include a distally-facing surface that be can be a conical surface, and the extraction guide distal opening can be at the center of the cone. The distally-facing surfaces can also be curved surfaces converging to the extraction guide distal opening 321.

Figure 3A:
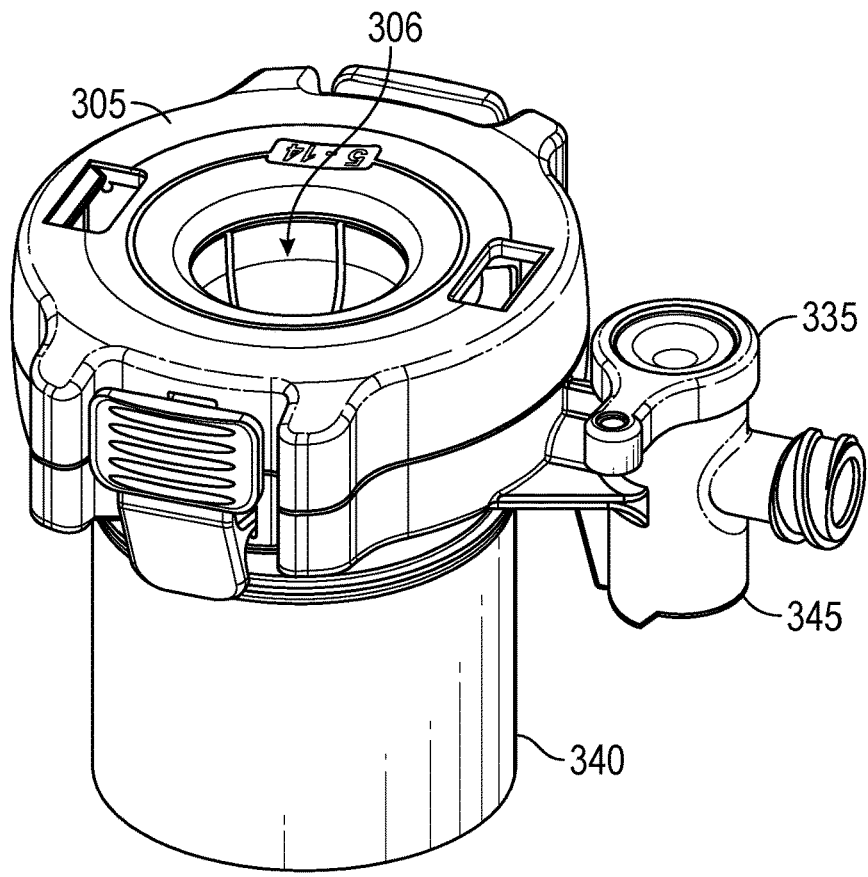
FIG. 3A is a perspective view of an example seal assembly.
Figure 3B:
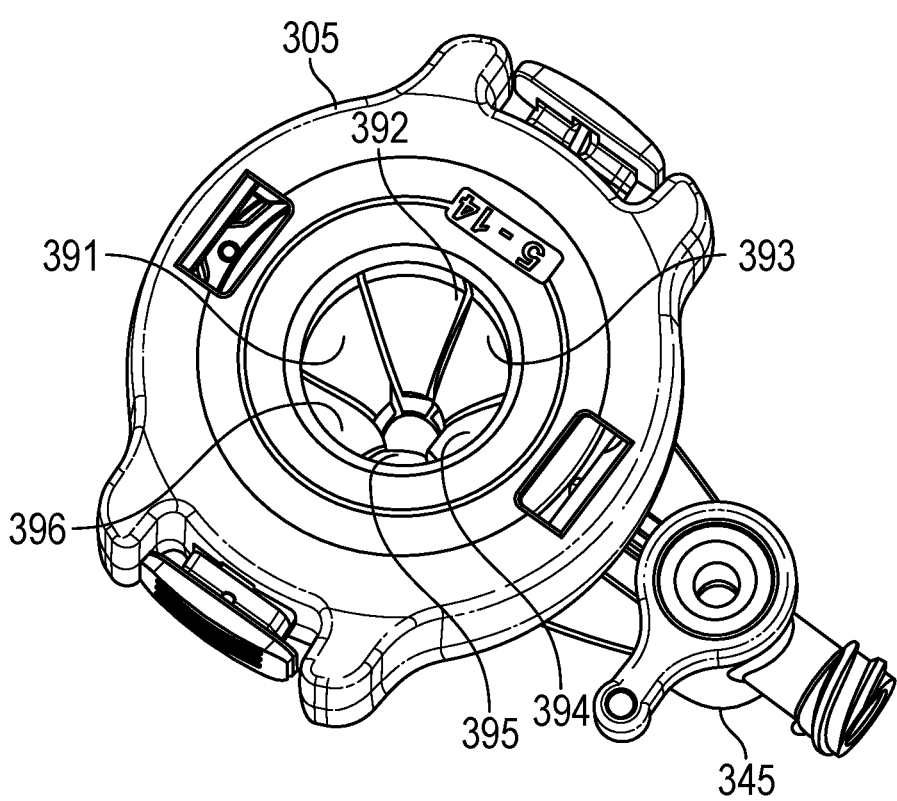
FIG. 3B is a top perspective view of an example seal assembly.
Figure 3C:
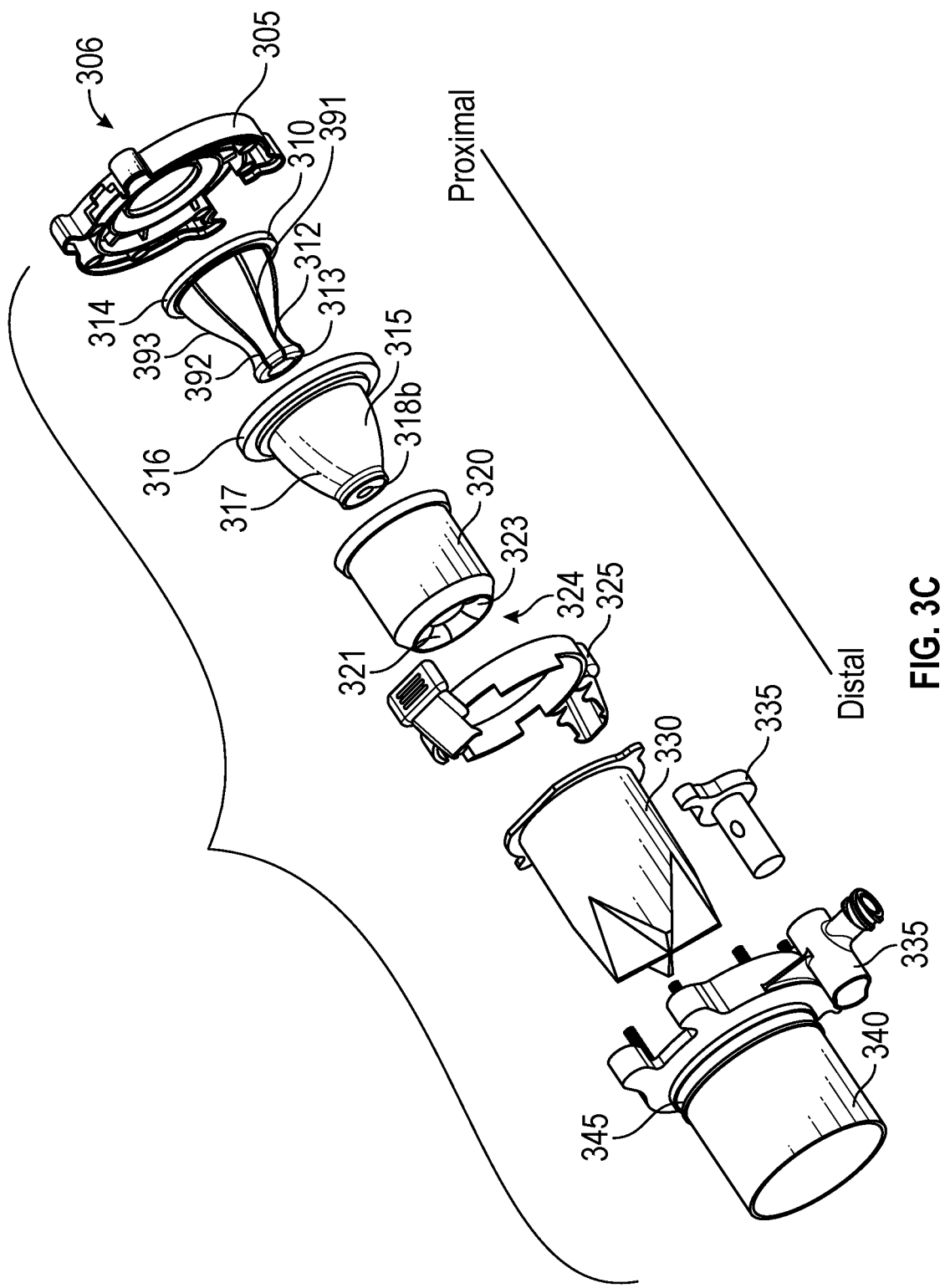
FIG. 3C is an exploded view of an example seal assembly.
Figure 3D:
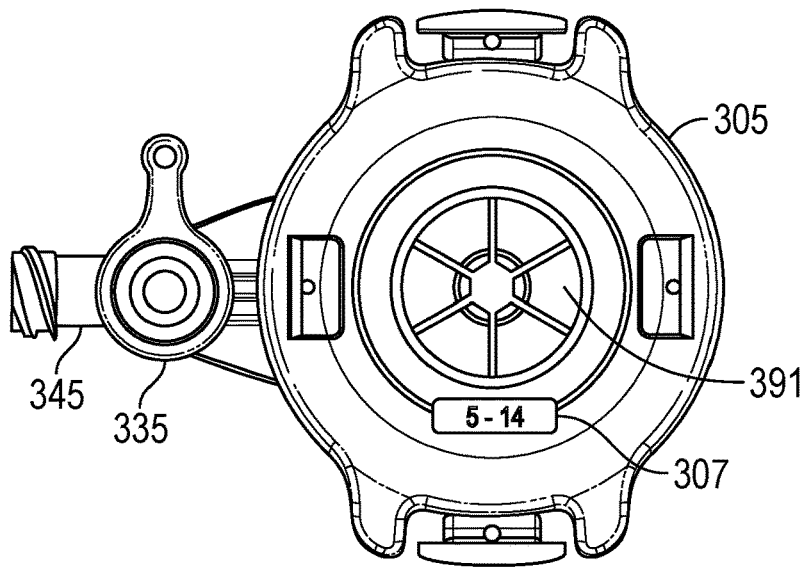
FIG. 3D is a top view of an example seal assembly.
Figure 3E:
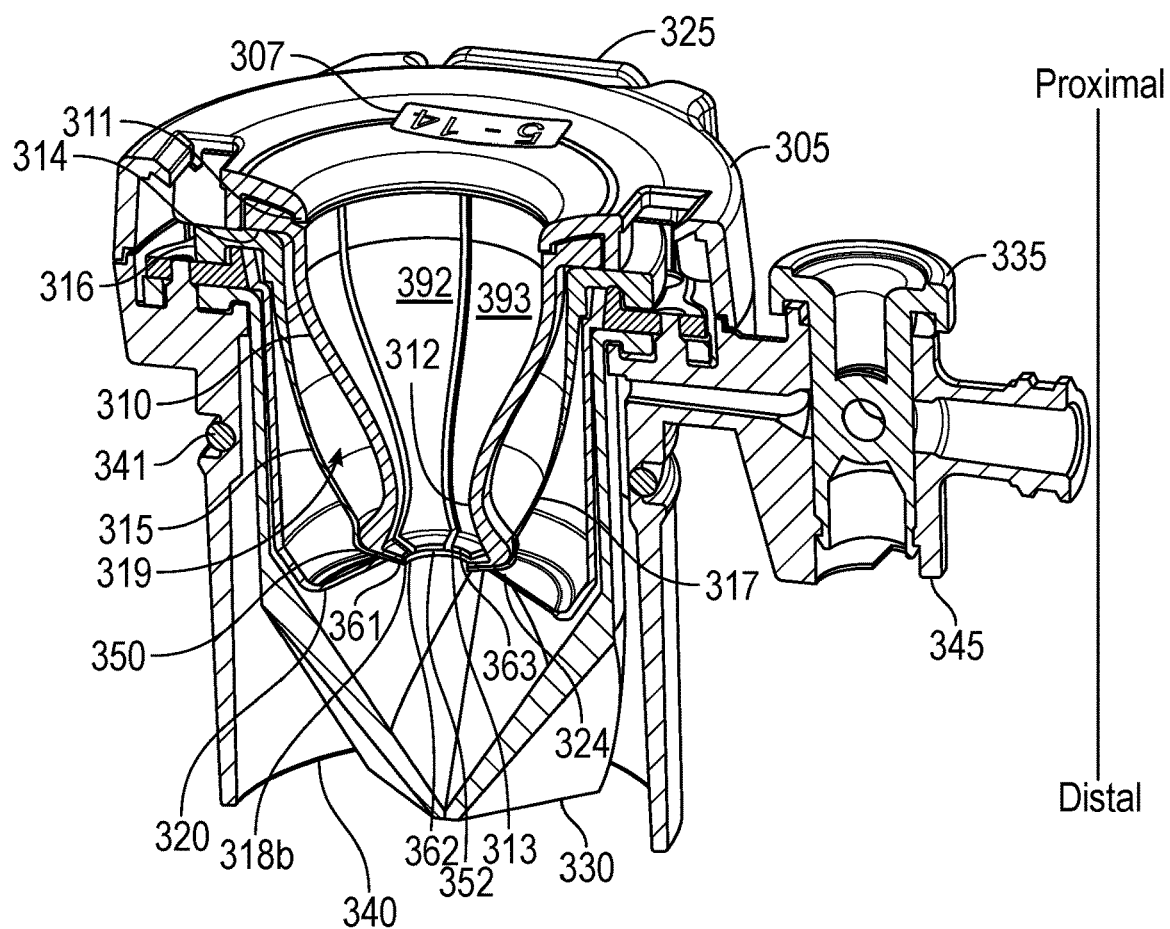
FIG. 3E is a perspective cross-sectional view of an example seal assembly.

The retraction guide 320 can include flanges or teeth 324 that form the tapered or concave distal surfaces. The teeth 324 can deflect or bend distally to accommodate insertion of an instrument that is larger than the distal opening in the extraction guide. The teeth 224 can return to their original configuration—defining a tapered or concave surfaces—when the instrument shaft 353 is withdrawn. When returned to the tapered or concave shape, the extraction guide can prevent snagging of an object, such as gauze, on the elongated members of the seal expander 310, when the object is pulled by a shaft through the assembly. The retraction guide 320 can at least partially fit inside the second seal 330, as shown in FIG. 3E.

The second seal 330 can be a "zero seal" that seals when no instrument in present in the seal assembly. The second seal can be a duck bill seal, for example, or a four-lipped "double duck bill" seal as shown in FIG. 3C. The second seal can also be a flapper valve (not shown), which can optionally be connected to a mechanism such as a lever or button that can be operated by a user to bias (i.e. opened and shut) the flapper valve.

The medical device seal assembly 300 can include a housing 340 that can include an O-ring for sealing with a sleeve or tube component (not shown). The housing can also include a gas port 345 which can be used for insufflation, and a manual valve 335 that can control the flow of gas through the gas port.

A clip 325 can connect to the housing 340 and the cap 305 to retain the components in an assembled configuration.

The openings in the cap 305, seal expander 310, first seal 315, retraction guide 320, and second seal 330 can be aligned with the axis 318c, so that an instrument can be received through the seal assembly 300, as illustrated in FIG. 2A. When an outer dimension (e.g., circumference) of an inserted instrument shaft is larger than an inside dimension of the neck portion 312 of the seal expander, the neck portion 312 of the seal expander can expand to accommodate the instrument.

Instrument shafts are typically circular in cross section. In an example, inner surfaces of the seal expander define a neck dimension diameter. When the outer diameter of an instrument shaft is larger than the inner diameter of the neck portion 312, the seal expander 310 can expand to a diameter that matches the outer diameter of the instrument shaft. For example, the inner diameter of the neck portion can be 5 millimeters (mm), and can be expandable up to 14 millimeters to accommodate a wide range (5-14 mm) of instrument shafts. The openings in the seal expander and seal can also be shaped as ovals, polygons (optionally with rounded corners) or other shapes, to accommodate similarly-shaped instrument shafts. The outer dimension of an inserted instrument can, for example, be the maximum dimension of non-circular shape, or a length of a major axis of an elliptical cross-section. Portions of the seal expander, such as fingers, can be individually-deflectable, so that the neck portion shape can change to match the shape and dimensions of a shaft.

Figure 3F:
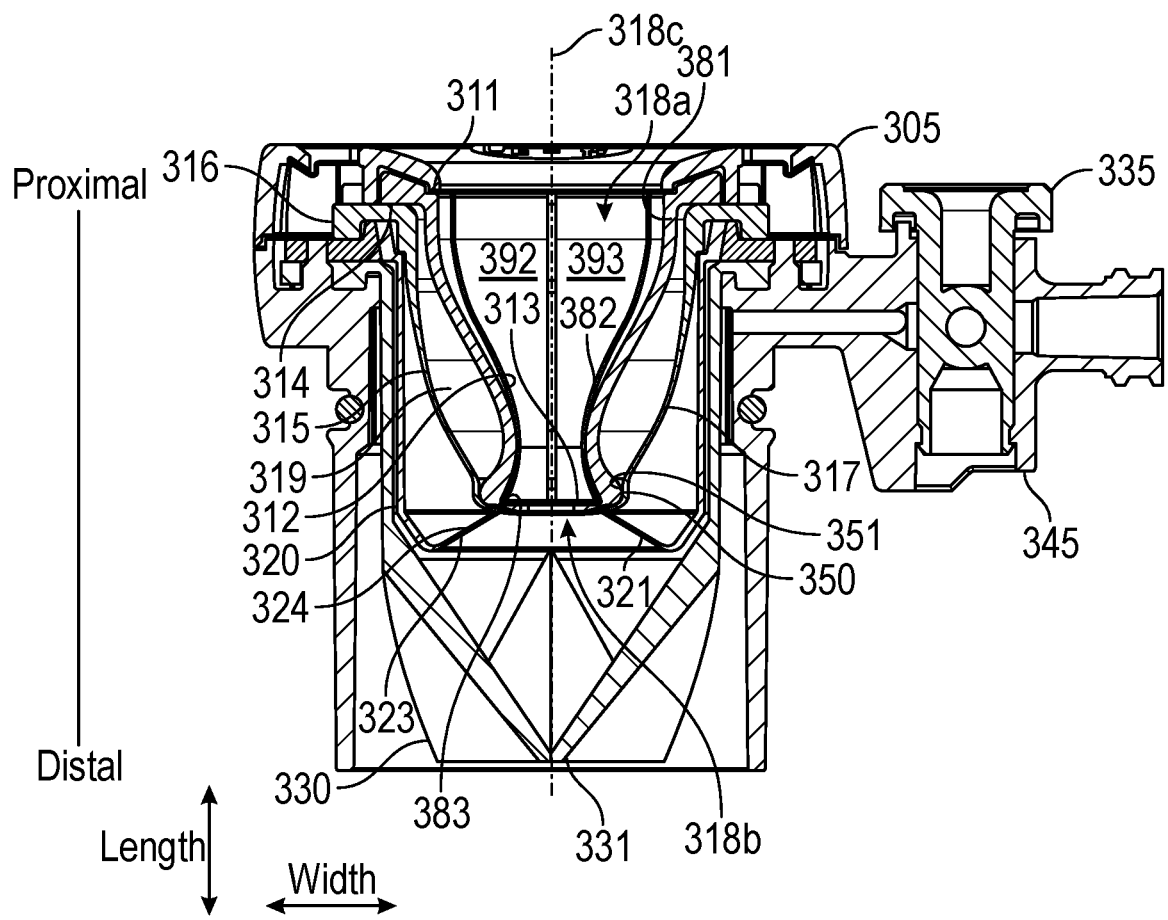
FIG. 3F is a cross-sectional view of an example seal assembly.
Figure 3G:
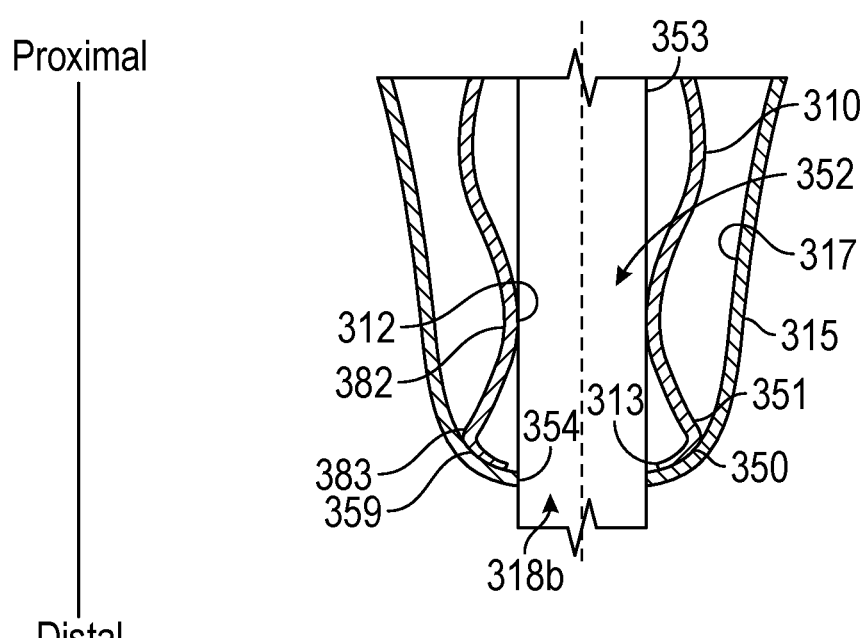
FIG. 3G is an enlarged cross-sectional view of a portion of the seal assembly of shown in FIG. 3F.

As shown in FIGS. 3E and 3F, and 3G, one or more distal outer surfaces 350 of the seal expander can interact with one or more inner surfaces 351 the first seal and cause the distal opening 318b to expand when a shaft is inserted through the neck portion 312 of the seal expander 310. The seal expander 310 can, for example, be sized and shaped so that as the neck portion expands, the distal opening 318b in the seal 315 is always smaller than the opening in the neck portion. This can assure that the seal 315 remains in contact with an outer surface of an instrument shaft that expands the neck portion 312 to the size of instrument shaft.

As shown in FIG. 3G, when an instrument shaft 353 that is larger than an opening 352 defined by the neck portion 312 of the seal expander 310, the outer surfaces 350 of the seal expander can define a seal interface portion 359 that can convey expansion forces on the one or more inner surfaces 351 of the first seal 315, which expands the size of the distal opening 318b in the first seal 315. The seal expander 310 and first seal 315 can be sized and shaped so that, as the distal opening is expanded, a sealing relationship is maintained between the instrument shaft 353 and the portions 354 of the first seal 315 that form the distal opening 318b.

In an example embodiment, in a neutral position, a diameter of the distal opening 318b in the first seal 315 can be slightly smaller, by an "offset dimension" than the diameter of the neck portion. This offset arrangement can assure that the instrument shaft 353 contacts the portions 354 of the first seal 315 that form the distal opening 318b, when the opening is expanded by the seal expander 310.

In another example, the seal expander can be sized and shaped so that the offset dimension changes, but is always positive as the distal opening expands through a range (e.g. 5-14 mm) of accommodated shaft sizes. In an example, the seal expander 310 and first seal 315 can be sized and shaped so that the offset dimension is constant, or is larger than a minimum value, as the seal expander expands the first seal 315 to accommodate an instrument shaft 353.

In an example embodiment, the seal expander can include a number of elongated segments or "fingers" 391, 392, 393, 394, 395, 396. As illustrated in FIG. 3B, the seal expander can, for example, include six elongated segments. The elongated segments can be about 0.03 inch (0.8 mm) thick, for example. Seal expanders with fewer or more elongated segments are also possible. For example, a seal expander with three, four or five segments is possible, and seal expanders with up to ten or more segments are also possible.

Each elongated segment 391, 392, 393, 394, 395, 396 can have a proximal portion 381, a middle portion 382, and a distal tip 383. In an example, each elongated segment of the plurality of elongated segments extends from the proximal portion 381 into the interior chamber 319 of the first seal 315, and toward the axis 318c of the interior chamber to the middle portion 382 of the elongated segment, and then further into the interior chamber 319 and away from the axis 318c of the interior chamber to the distal tip 383 of the elongated segment. Each distal tip 383 of each of the plurality of elongated segments can be positioned on or near the side wall 317 of the first seal 315. In an example, an instrument shaft can bias the elongated segments 391, 392, 393, 394, 395, 396 away from the axis 318c, which pushes the distal tips against the side wall 317 of the first seal and expands the distal opening 318b to accommodate the instrument shaft 353.

The distal mouth 313 of the seal expander can include flanges 361, 362, 363 that can extend inward from distal ends of the elongated segments, toward the axis 318c. The flanges can also converge distally, i.e. extend both toward the axis 318c and distally toward the distal end of the first seal 353.

The flanges 361, 362, 363 can support the seal 315 during retraction of an instrument, for example to avoid stretching of the seal as an instrument is retracted. In an example, the flanges 361, 362, 363 can reduce friction during retraction by providing structural support that prevents the seal from pulling or wrapping on an instrument shaft during retraction. In an example, the seal assembly provides for approximately consistent friction forces during insertion and retraction. The flanges can, for example, assure that the surface area of the seal 315 that is in contact with an instrument shaft during withdrawal is approximately the same as the surface area that is in contact with the instrument shaft during insertion. Without the flanges on the seal expander 310, the instrument shaft could, for example, pull the first seal 315 proximally as the shaft is withdrawn, which can increased frictional forces, due to increased surface area between the shaft and seal 315.

Figure 4A:
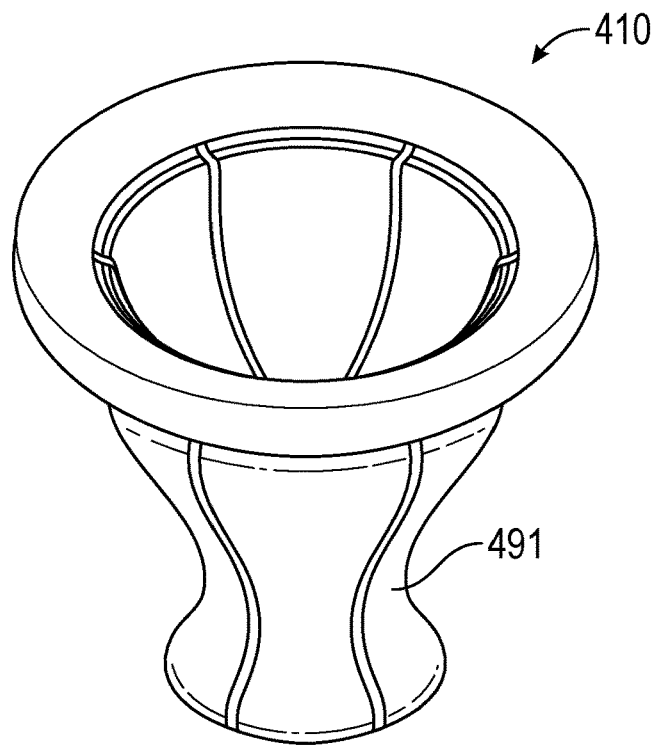
FIG. 4A is a perspective view of an example seal expander.
Figure 4B:
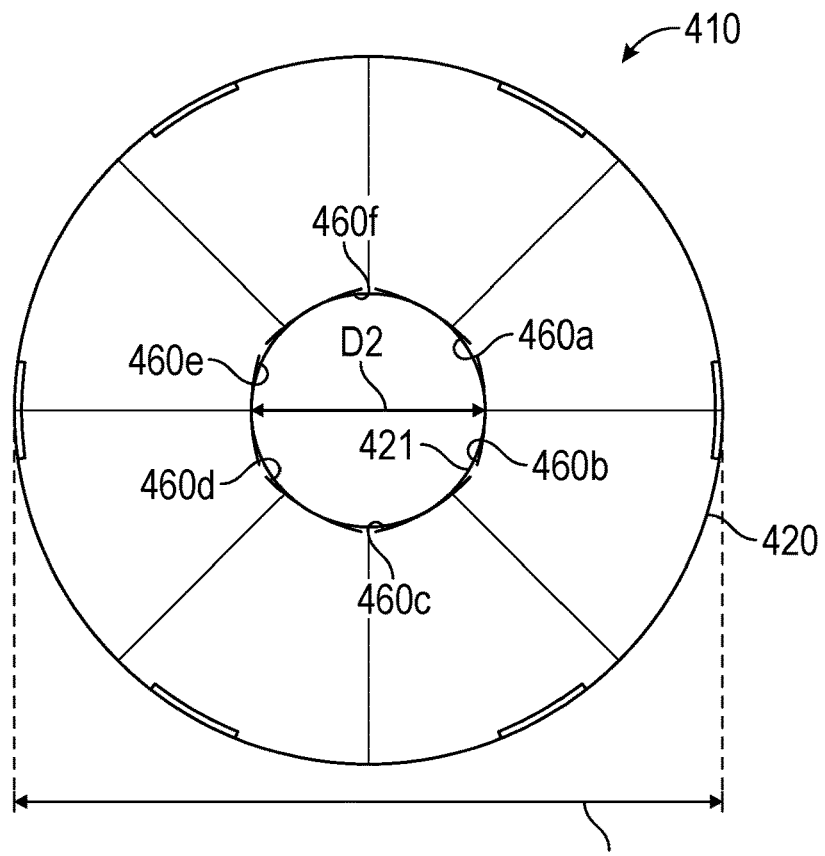
FIG. 4B is a conceptual illustration of an end view of the example seal expander shown in FIG. 4A.

FIGS. 4A-4D are show an example seal expander 410 that can be part of an expandable seal assembly, such as the seal assembly 300 illustrated in FIGS. 3A-F. FIG. 4A is a perspective view of an example seal expander 410. FIG. 4B is a conceptual illustration that shows a shape of instrument contacting surfaces 460a, 460b, 460c, 460d, 460e, 460f on a neck portion 412 of the seal expander 410 in a neutral state and an expanded state. The surfaces 460a-f can be shaped so that in an expanded state they align with a circle 420 having a diameter D1, which can, for example, be the diameter of the largest compatible instrument shaft 450 for the expandable seal assembly. In a neutral state, the surfaces 460a-f can be tangent with a circle 421 having a diameter D2 that is smaller than D1.

Figure 4C:
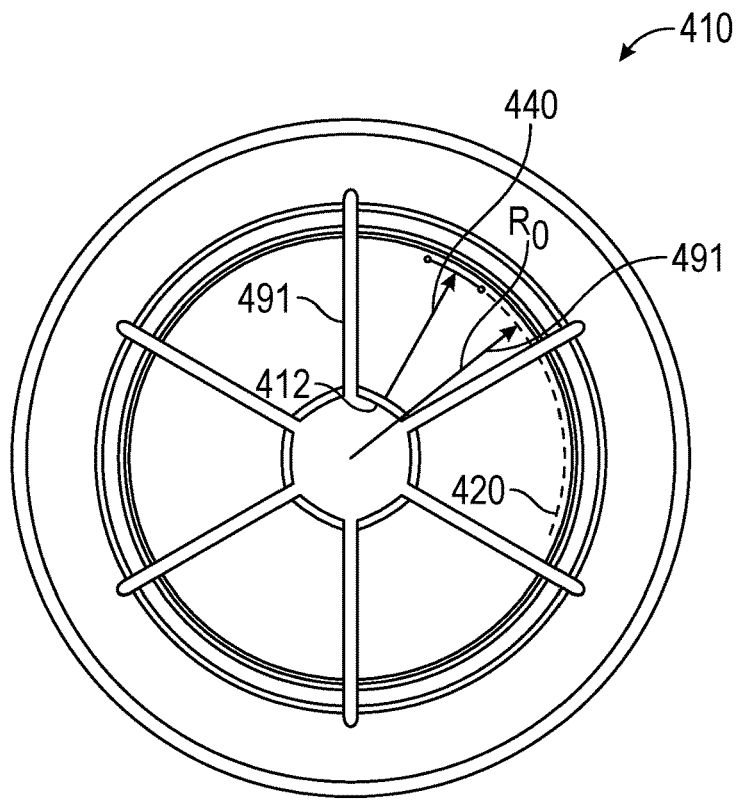
FIG. 4C is a top view of the example seal expander shown in FIG. 4A.

FIG. 4C is a top view of the seal expander 410 and illustrates an arrangement similar to FIG. 4B. The arrow 440 indicates the expansion of elongated segment 491 to a maximum expanded state, at which point the radius of curvature 480 of the neck portion 412 matches the radius $R_i$ of the circle 420 at the maximum expanded state.

Figure 4D:
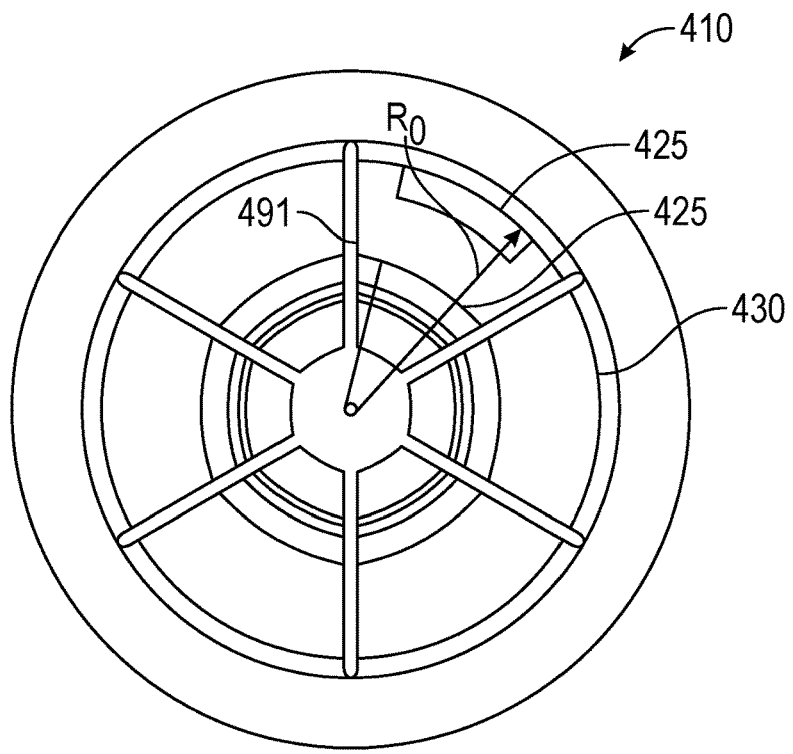
FIG. 4D is a bottom view of the example seal expander shown in FIG. 4A.

FIG. 4D is a bottom view of the seal expander 410 in a neutral state. FIG. 4D shows that the radius of curvature of the outer surface 425 of the elongated segment 491 matches the radius $R_o$ of a circle 430 at the maximum expanded state of the elongated segment 491.

Figure 4E:
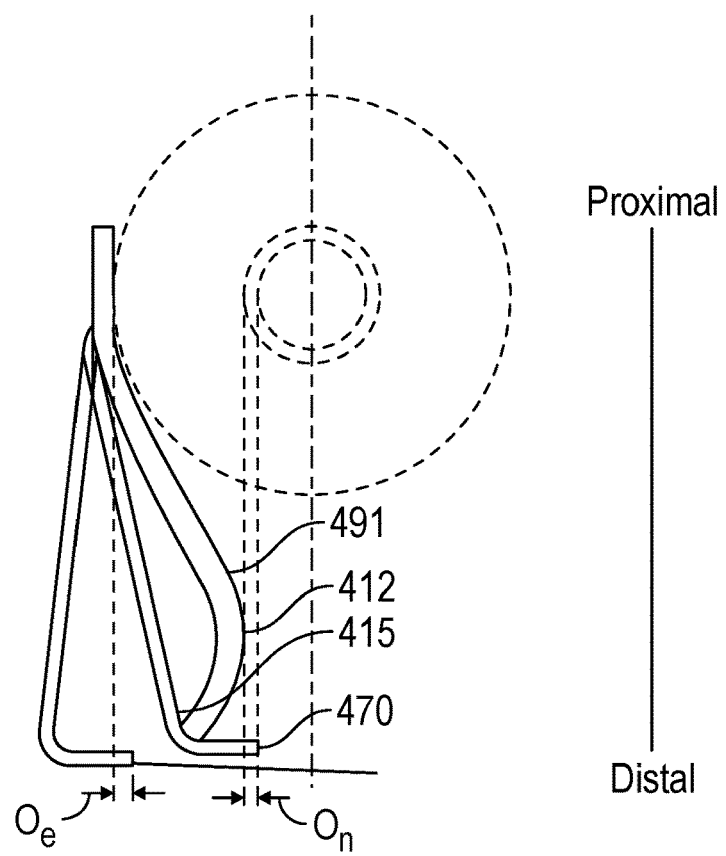
FIG. 4E is an illustration of an example configuration of an elongated segment of a seal expander and a portion of a wiper seal.

FIG. 4E illustrates an example configuration of the seal expander 410 and seal 415. An elongated segment 491 has a neck portion 412 that, in a neutral position has inner surfaces having a minimum dimension. An neutral offset dimension $O_n$ can be defined between the neck portion 412 and the wiper portion 470. When an instrument is inserted in the seal assembly, it deflects the elongated segment 491' to a deflected position at which point an expanded offset dimension $O_c$ can be defined between the neck portion and the wiper portion. In an example, the expanded offset dimension $O_n$ is approximately the same as the neutral offset dimension $O_n$. In another example, the expanded offset dimension is within a predetermined percentage of the neutral offset dimension (e.g. within 10%, within 15%, or within 20% of the neutral offset dimension.)

Figure 5A:
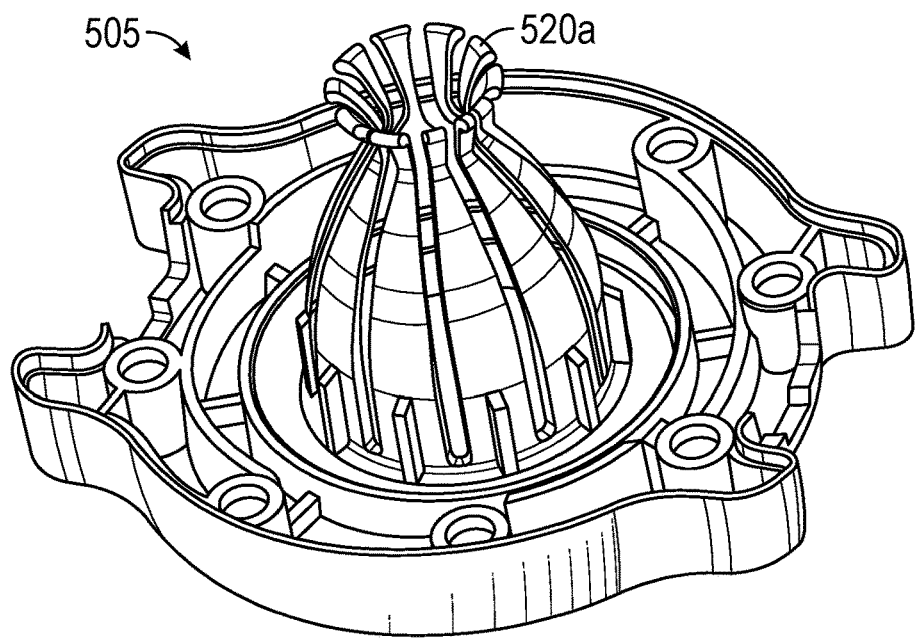
FIG. 5A is a perspective view of a seal expander connected to a cap.

FIG. 5A shows an example in which a seal expander 510 is connected to a cap 505. For example, a seal assembly can be provided that includes the cap 505 and seal expander 510 as a single piece. The example seal expander 510 is shown with ten elongated segments, but seal expanders could include more, or fewer elongated segments.

Figure 5B:
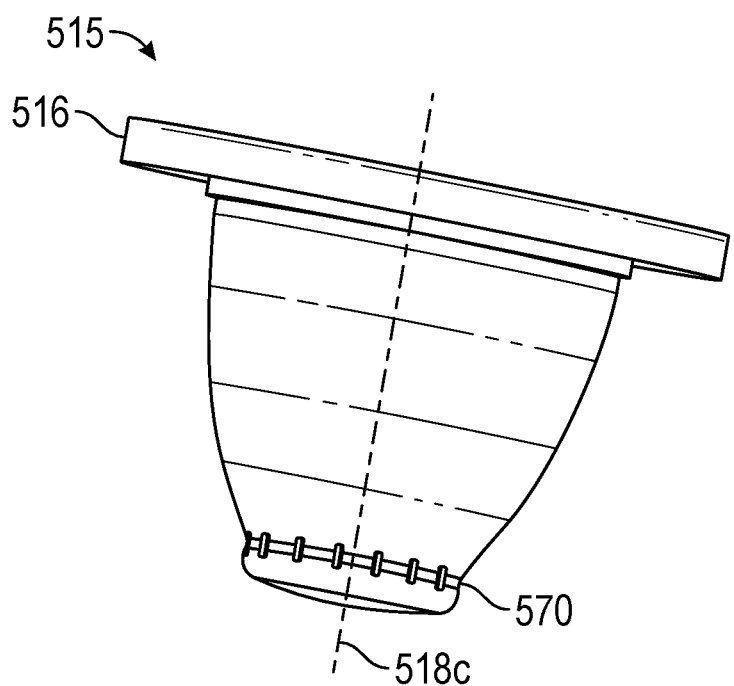
FIG. 5B is a side view of an example first seal that can interact with a seal expander as part of an expandable seal assembly.

FIG. 5B is a side view of an example first seal 515 that includes a lip 516 and an interrupted cinch 570. The interrupted cinch 570 can provide circumferential strength to provide tension during expansion of the seal 515. The tension can, for example, assure that an effective seal is maintained against an instrument shaft inserted through opening in the seal.

Figure 5C:
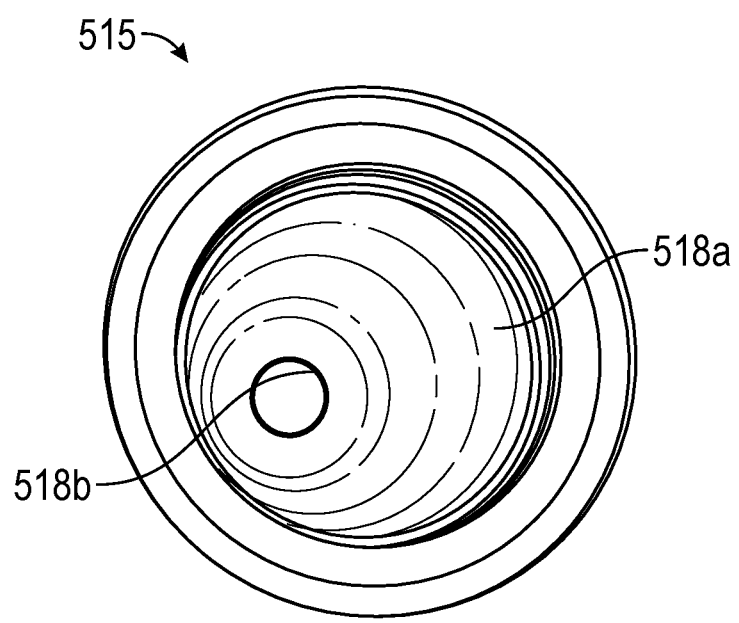
FIG. 5C is a top perspective view of an example first seal that can interact with a seal expander as part of an expandable seal assembly.

FIG. 5C is a perspective top view of the first seal 515 that shows the proximal opening 518a and distal opening 518b which can define an axis 518c, shown in FIG. 5B.

Figure 5D:
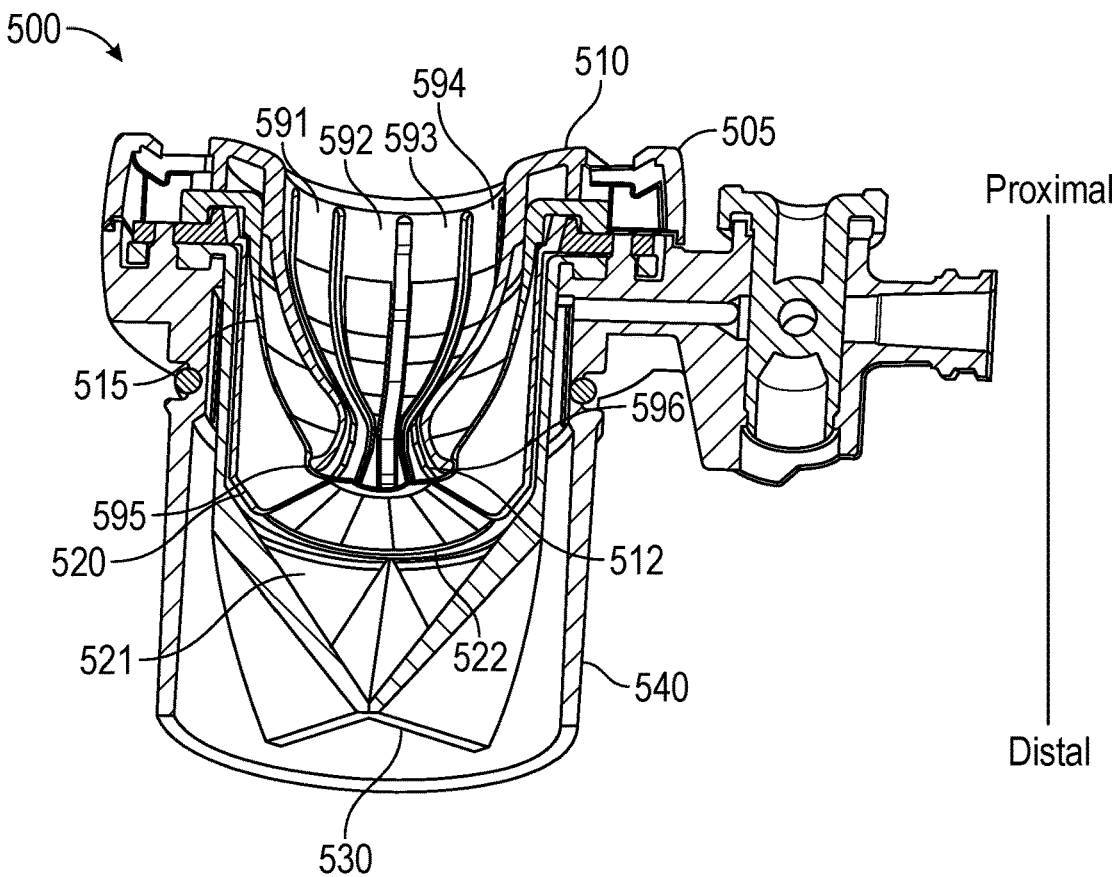
FIG. 5D is a perspective cross-sectional view of an example seal assembly.

FIG. 5D is a perspective cross-sectional view of an example seal assembly 500 that shows the cap and seal expander 510 assembled with the first seal 515, a retraction guide 520, second seal 530, and housing 540. The retraction guide 520 can have a plurality of teeth 522 that can guide an awkwardly-shaped object such as gauze to the distal opening 51 in the first seal 515. The seal guide can have a number of elongated segments or "fingers" 591, 592, 593, 594 (and additional segments that are not shown in the cross-section) that can expand when an instrument is inserted into the seal assembly 300, which biases the distal ends 595, 596 of the elongated members against the seal 515 and expands the distal opening 521.

Figure 6A:
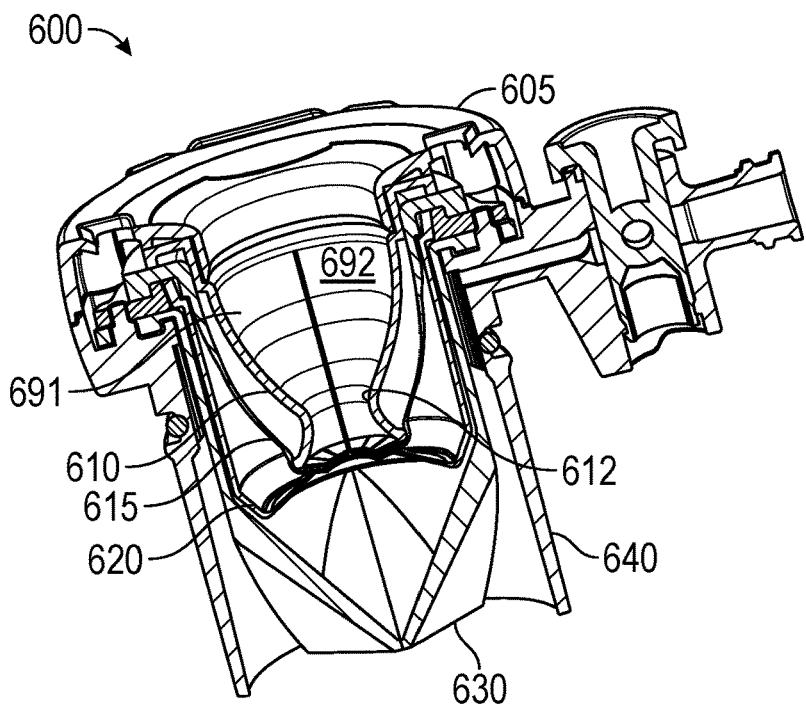
FIG. 6A is a perspective cross-sectional view of an example seal assembly without a retraction guide.

FIG. 6A is a cross-sectional view of another example expandable seal assembly 600 that include a cap 605, seal expander 610 having elongated segment 691, 692, a first seal 615, retraction guide 620, second seal 630, and housing 640. The seal expander 610 in this example has four elongated segments, two of which 691, 692 appear in the cross-section figure. The elongated segments converge to define a neck portion 612. Inner surfaces at the neck portion define a neck diameter.

Figure 6B:
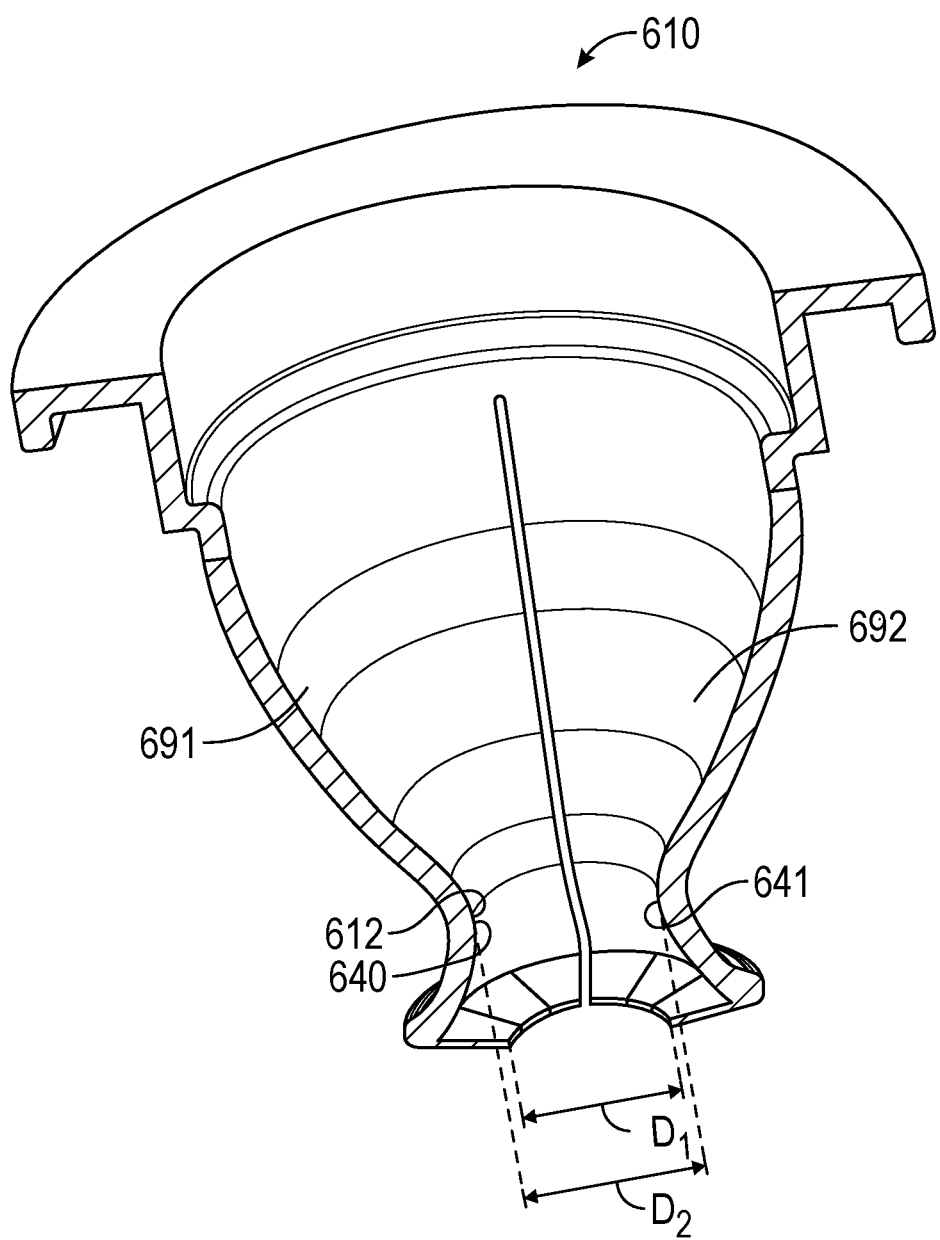
FIG. 6B is a perspective cross-sectional view of an example seal expander with flanges in a neutral position.
Figure 6C:
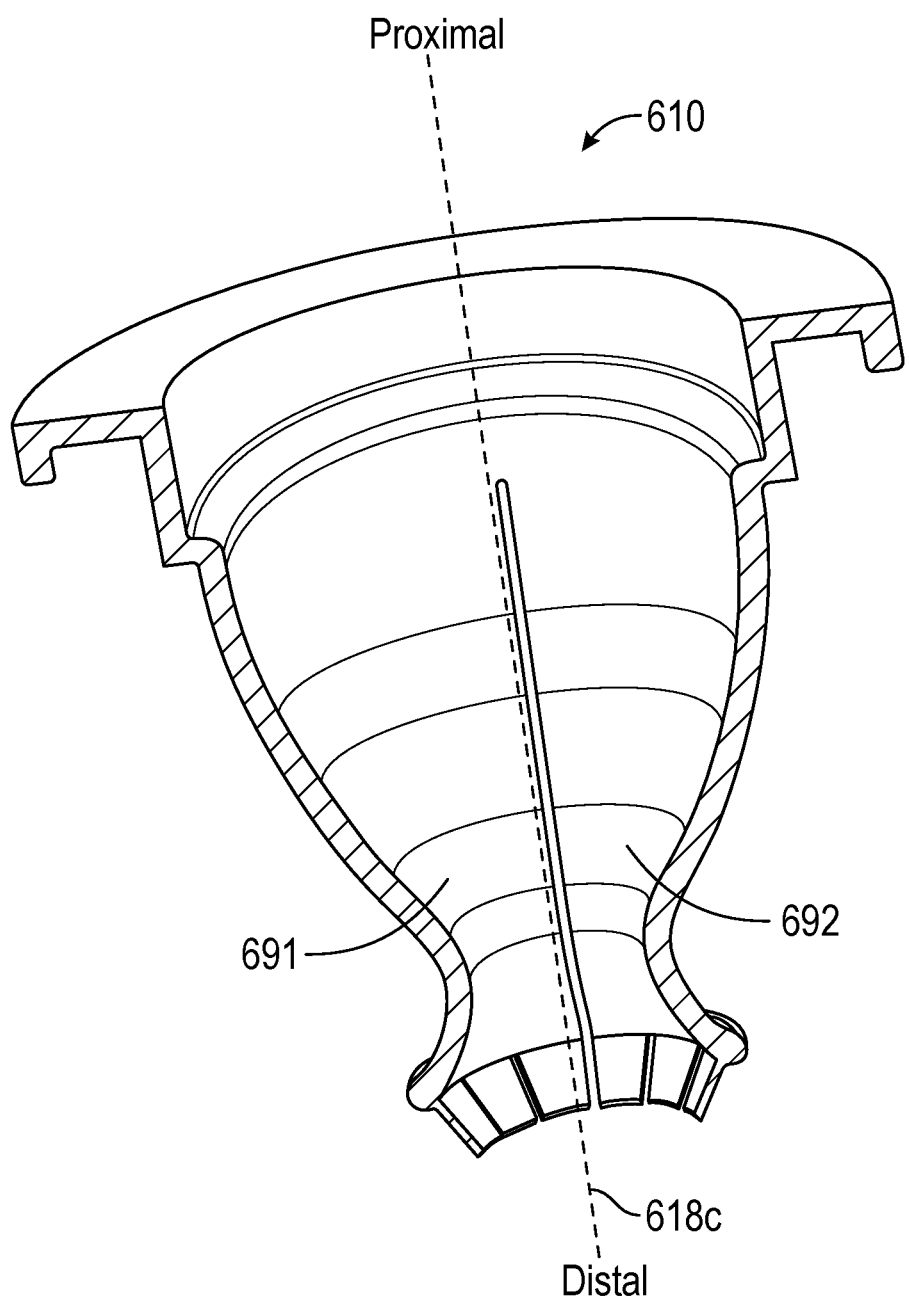
FIG. 6C is a perspective cross-sectional view of an example: seal expander with flanges in a distally-deflected position.

FIG. 6B and FIG. 6C show the seal expander 610 in a first state and a second state. In the first state, the flanges 681, 682, 683, 684, 685, 686 are in a neutral position. In the second state, shown in FIG. 6C, the flanges 681, 682, 683, 684, 685, 686 are deflected distally to accommodate an instrument (not shown) that is inserted through the seal expander. When the instrument is larger than the diameter D1 defined by the flanges, but smaller than the diameter D2 defined by inner surfaces 641, 642 of the neck portion 612, the flanges deflect as the instrument is inserted, as shown in FIG. 6C. When the instrument is larger than the diameter D2 of the neck portion (not shown), the elongated segments 691, 692 deflect outward away from an axis 618c of the seal expander.

Figure 7:
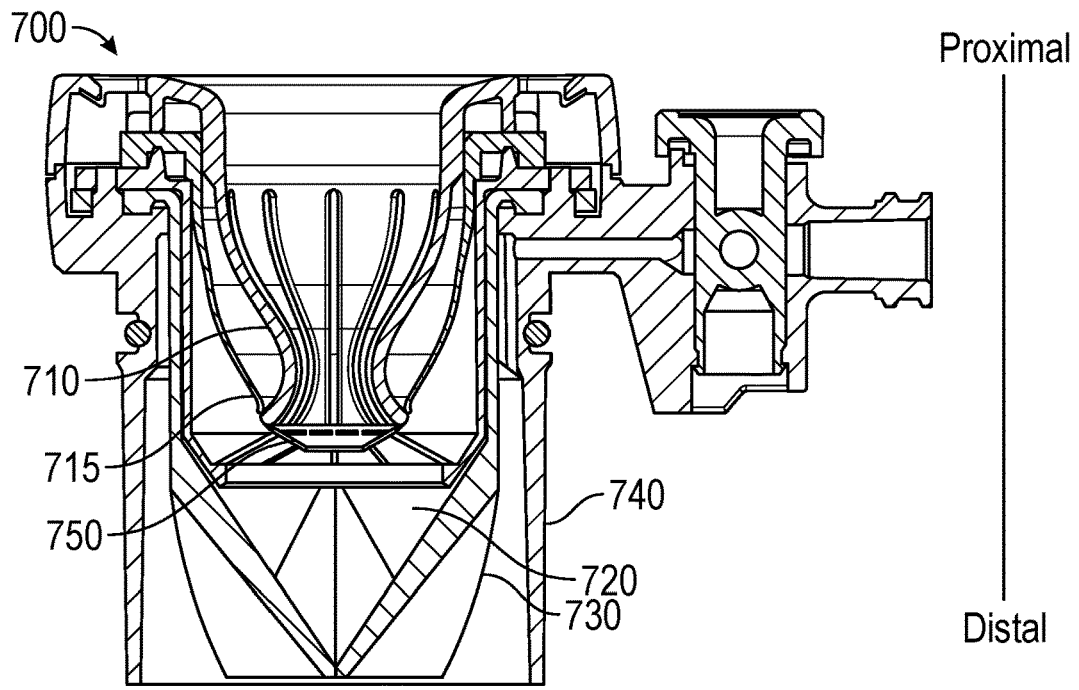
FIG. 7 is a cross-sectional view of an example seal assembly with an elongated first seal.

FIG. 7 is a cross-sectional view of another example expandable seal assembly 700 that includes a seal expander 710, first seal 715, retraction guide 720, second seal 730, and housing 740. The first seal 715 has a tapered portion 750 that decreases in radius distally. The seal expander 710 has elongated segments that contact an inner surface of the first seal 715 proximal of the tapered portion 750. The tapered portion 750 of the first seal 715 can extend into the retraction guide 720. When an object is retracted, the tapered portion 750 of the first seal can invert, and extend proximally into the seal expander.

FIG. 8 is a cross-sectional view of example expandable assembly 800 that includes an expander 810 and a retraction guide 820. The expander can include a neck portion 812 and elongated segments 891, 892, 893, 894, 895, 896. The retraction guide can include elongated segments, 881, 882, 883, 884. The elongated segments can each define a pocket 885, 886 which can receive a distal end 861, 862 of the elongated segments 891, 892. In an example, the elongated segments 881, 882, 883, 884 of the retraction guide can expand and retract with the elongated segments 891, 892, 893, 894, 895, 896 of the expander. For example, when an instrument shaft (not shown) in inserted through the neck portion 812 of the expander, the elongated segments 891, 892, 893, 894, 895, 896 deflect away from an axis 818c of the expander. The expanded elongated segments 891, 892, 893, 894, 895, 896 can push against the elongated segments 881, 882, 883, 884 of the retraction guide and bias the elongated segments of the retraction guide away from the axis to accommodate the instrument shaft. The assembly 300 is shown in FIG. 8 without a seal between the expander and the retraction guide. In another example, a seal can be added to the configuration shown in FIG. 8, positioned between the expander and the retraction guide, with a sealing surface configured to seal against an instrument shaft, as shown for example in FIG. 3C and FIG. 6A.

FIG. 9 is a cross-sectional view of an expandable seal assembly 900 that includes a seal expander 910 and a first seal 915. The seal can include a tapered portion 920 as explained above in reference to FIG. 7. In this example, the assembly does not include a retraction guide. The seal expander can include elongated segments 991, 992 that have distal surfaces that flare outwardly away from an axis 918c to define a distally-facing mouth 925. The distally-facing mouth can act as an extraction guide, to guide objects into the seal 915.

FIG. 10 is a cross-sectional view of an expandable seal assembly 1000 includes a seal expander 1010 and a first seal 1015. The seal expander 1015 can include elongated segments 1091, 1092 that vary in thickness along the length and define a neck portion 1012. The elongated segments 1091, 1092 can have distal surfaces that define a distally-facing mouth 1025. The distally-facing mouth can act as an extraction guide.

Figure 11A:
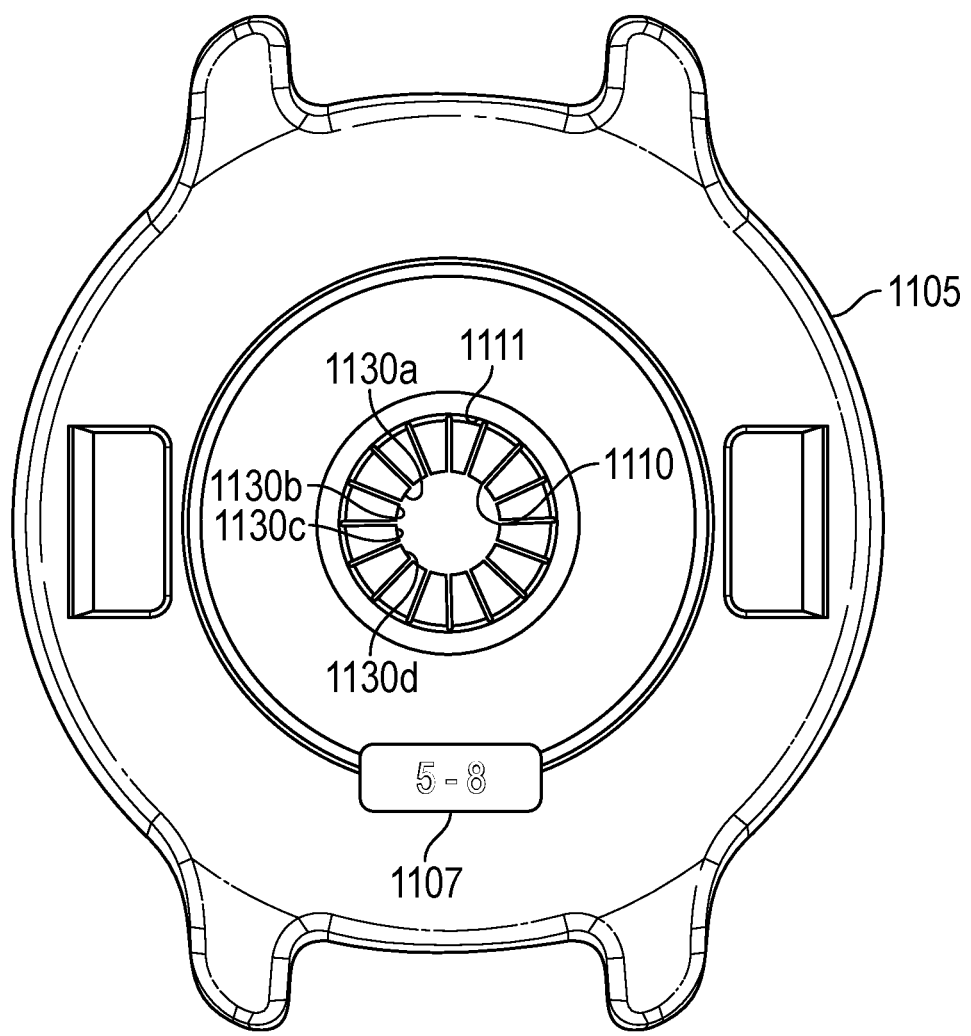
FIG. 11A is a top view of an example seal assembly.
Figure 11B:
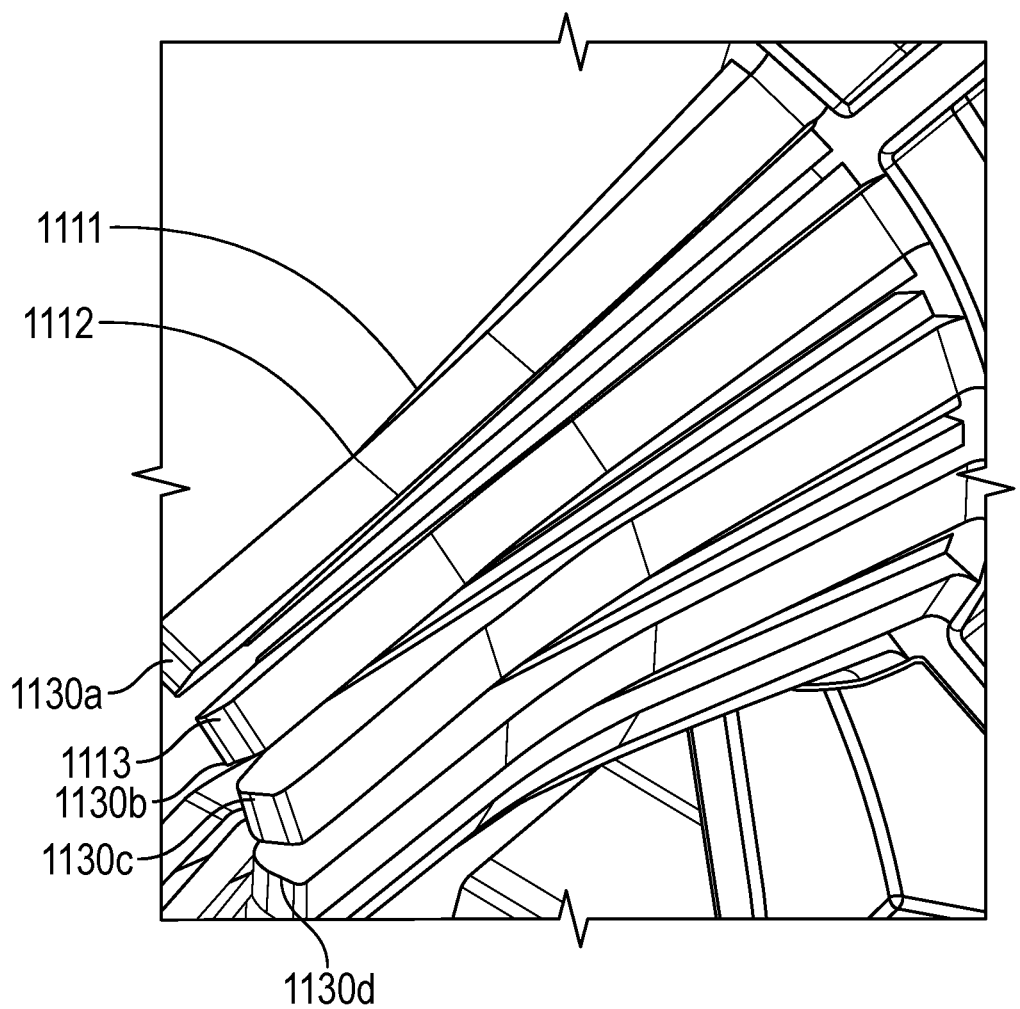
FIG. 11B is a bottom perspective view of an example seal assembly.
Figure 11C:
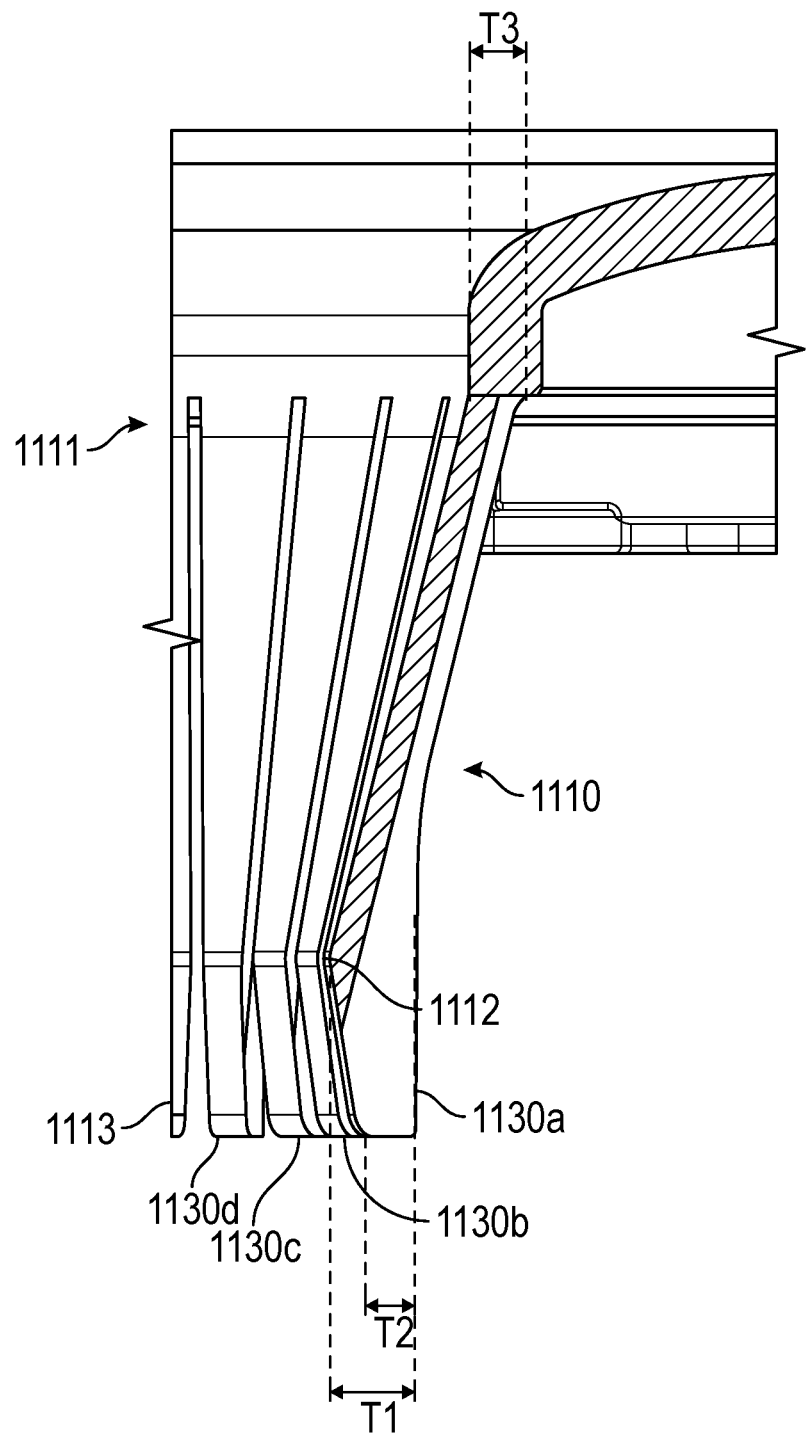
FIG. 11C is a partial cross-sectional view of the example seal assembly shown in FIGS. 11A and 11B.

FIG. 11A is a top view of an example cap 1105 and seal expander 1110. FIG. 11B is a bottom partial perspective view of an example seal expander 1110. FIG. 11C is a partial cross-sectional view of the example seal assembly shown in FIGS. 11A and 11B. The seal expander 1110 can be connected to the cap 1105, or a fabricated separated piece that is directly or indirectly coupled to the cap 1105. The cap 1105 and seal expander 1110 can be sized and shaped to accommodate a range of shaft sizes. For example the cap 1105 and seal expander shown in FIGS. 11A and 11B can be sized and shaped to accommodate shafts or tool ranging from 5 to 8 millimeters. The cap can include a label 1107 that indicates the range of sizes. The seal expander 310 can include a proximal opening 1111, an expandable neck portion 1112, and a distal mouth 1113. In an example, configuration, the proximal opening 1111, expandable neck portion 1112, and distal mouth 1113 can be shaped similar to the arrangement shown in FIGS. 3F and 3G. The seal expander can include a plurality of elongated segments or "fingers" 1130a, 1130b, 1130c 1130d that can be deflectable to accommodate a shaft inserted through the seal expander and expand a seal (not shown) surrounding the seal expander. In an example configuration, the elongated segments 1130a, 1130b, 1130c 1130d can converge at the neck portion 1112 and flare outward toward a mouth that is larger than the neck. The elongated segments 1130a, 1130b, 1130c 1130d can be have a radial thickness $T_1$ that is larger at the neck 1112 than a thickness $T_2$ at the mouth 1113 and larger than a segment thickness $T_3$ at the mouth.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A medical device seal assembly comprising:
a housing;
a first seal inside at least part of the housing, the first seal having a side wall that surrounds and defines an interior chamber, an expandable portion that joins a distal end of the side wall, a first opening at a proximal end of the interior chamber, and an expandable seal opening in the expandable portion, an axis of the interior chamber being defined between the first opening and the expandable seal opening;
a plurality of elongated segments that extend distally into the interior chamber of the first seal, each elongated segment of the plurality of elongated segments having a proximal portion, a middle portion, and a distal tip, each elongated segment of the plurality of elongated segments extending from the proximal portion into the interior chamber and toward the axis of the interior chamber to the middle portion, each elongated segment of the plurality of elongated segments extending from the middle portion further into the interior chamber and away from the axis of the interior chamber to the distal tip, and each distal tip of each of the plurality of elongated segments being positioned on or near the side wall of the first seal;
a second seal distal of the first seal; and
an extraction guide between the first seal and the second seal, at least a portion of the extraction guide being inside the second seal, and at least a portion of the first seal extending inside the extraction guide.

2. The medical device seal assembly of claim 1, wherein:
the middle portions of the plurality of elongated segments converge to define a neck; and
the neck has a minimum internal neck dimension.

3. The medical device seal assembly of claim 2, wherein the minimum internal neck dimension is less than an outer cross-sectional dimension of an instrument shaft such that the instrument shaft inserted through the plurality of elongated segments is configured to bias the plurality of elongated segments away from the axis of the interior chamber to press against the side wall of the first seal and expands the expandable portion of the first seal and the seal opening.

4. The medical device seal assembly of claim 1, wherein:
each elongated segment of the plurality of elongated segments has a segment length in a proximal to distal direction and a segment width that varies along the length of the elongated segment;
a minimum segment width is at the middle portion of the elongated segment; and
a maximum segment width is in the proximal portion of the elongated segment.

5. The medical device seal assembly of claim 1, wherein the plurality of elongated segments are arranged concentrically around the axis of the interior chamber.

6. The medical device seal assembly of claim 1, wherein:
the extraction guide includes a distally-facing concave surface and an extraction guide opening in the distally-facing concave surface; and
the extraction guide opening is aligned with the expandable seal opening in the first seal.

7. The medical device seal assembly of claim 1, wherein each elongated segment of the plurality of elongated segments further includes at least one flange that is connected to the distal tip and extends inward toward the axis of the interior chamber.

8. A medical device comprising:
a housing;
a first seal structure having a proximal end and a distal end, the first seal structure being at least partially inside the housing, the first seal structure including a side wall surrounding and defining an interior chamber, a seal wall connected to the side wall, a first opening at a proximal end of the side wall, and an expandable opening in the seal wall, an axis of the interior chamber being defined between the first opening and the expandable opening;
a seal expander coupled to the housing and at least partially in the interior chamber of the first seal structure, the seal expander including an expandable neck portion and a seal interface portion, an internal size of the seal expander increasing from the expandable neck portion to the seal interface portion, and the seal interface portion being near an intersection of the side wall and the seal wall;
a second seal structure coupled to the housing; and
an extraction guide, at least a portion of the extraction guide being inside the second seal structure, and at least a portion of the first seal structure extending inside the extraction guide.

9. The medical device of claim 8, wherein the seal interface portion interfaces with the side wall at an angle perpendicular to the axis.

10. The medical device of claim 8, wherein:
in a first state, the neck portion of the seal expander is in an expanded state to accommodate a shaft portion of an instrument, the neck portion including one or more internal surfaces defining a first internal profile having an expanded internal size to accommodate an outer surface of the shaft portion of the instrument, the seal interface portion of the seal expander being pressed against the side wall of the first seal structure, and the expandable opening in the seal wall being expanded to an expanded opening size; and
in a second state, the neck portion of the seal expander is in a neutral state, the internal surfaces of the neck portion defining a second internal surface profile having a neutral internal size that is smaller than the expanded internal size, and the expandable opening in the seal wall having a second opening size that is smaller than the expanded opening size.

11. The medical device of claim 8, wherein:
the extraction guide includes a distally-facing surface and an extraction guide opening in the distally-facing surface;
the distally-facing surface is distal of the expandable opening in the seal wall of the first seal structure and includes portions sized and shaped to guide an object to the extraction guide opening; and the extraction guide opening is aligned with the axis of the interior chamber.

12. The medical device of claim 8, wherein:
the seal expander includes a plurality of elongated elements that extend distally into the first seal structure, converge to form the neck portion, and extend from the neck distally and outwardly away from the axis of the interior chamber; and
each of the elongated elements has one or more distal surfaces comprising the seal interface portion of the seal expander.

13. A medical device comprising:
a first seal having a side wall, a seal portion connected to the side wall, an interior chamber defined by the side wall, and a seal opening defined in the seal portion;
a plurality of elongated segments extending into the interior chamber of the first seal, the plurality of elongated segments extending to converge at an intermediate neck and then extending to diverge at a distal mouth, a minimum internal dimension of the intermediate neck being less than a minimum internal dimension of the distal mouth, each elongated segment of the plurality of elongated segments having a distal end;
a second seal distal of the first seal; and
an extraction guide at least partially in the second seal;
wherein expansion of the intermediate neck biases the distal ends of the plurality of elongated segments radially outward against the side wall of the first seal and increases a size of the seal opening; and
wherein the first seal is at least partially in the extraction guide.

14. The medical device of claim 13, wherein:
the medical device further comprises a base portion; and
each of the plurality of elongated segments is coupled to the base portion by one or more hinge portions and pivots at the one or more hinge portions when the neck is expanded.

15. The medical device of claim 13, wherein:
the medical device further comprises a cannula cap and a cannula coupled to the cannula cap; and
the second seal is at least partially in the cannula.

16. The medical device of claim 13, wherein:
the seal opening is circular and has a seal opening diameter;
the intermediate neck defines a circular opening having a neck inner diameter; and
the seal opening diameter smaller than the neck inner diameter.

17. The medical device of claim 13, wherein:
a difference between a diameter of the seal opening and an inner diameter of the neck defines a seal offset dimension; and
the plurality of elongated segments are sized and shaped to provide a consistent seal offset dimension seal through a range of expanded states to accommodate a range of sizes of shafts inserted through the plurality of elongated segments.

18. The medical device of claim 13, wherein:
in a first state, the plurality of elongated segments and the seal portion are in an expanded state to accommodate a shaft portion of an instrument, and a difference between a diameter of the seal opening in the expanded state and an inner diameter of the neck defines a first state offset dimension;
in a second state, the plurality of elongated segments and the seal portion are in a neutral state, and a difference between the diameter of the seal opening in the neutral state and the inner diameter of the neck defines a second state offset dimension; and
the first state offset dimension is approximately the same as the second state offset dimension.

* * * * *

UNITED STATES PATENT AND TRADEMARK OFFICE
CERTIFICATE OF CORRECTION

PATENT NO. : 10,980,952 B2
APPLICATION NO. : 15/592910
DATED : April 20, 2021
INVENTOR(S) : Wixey et al.

Page 1 of 1

It is certified that error appears in the above-identified patent and that said Letters Patent is hereby corrected as shown below:

In the Claims

In Column 18, Line 10, in Claim 16, after "diameter", insert --is--

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*